United States Patent
Jenkins et al.

(10) Patent No.: US 10,207,021 B2
(45) Date of Patent: Feb. 19, 2019

(54) LOW SWELL TISSUE ADHESIVE AND SEALANT FORMULATIONS

(71) Applicant: Actamax Surgical Materials, LLC, Berkeley, CA (US)

(72) Inventors: Lauri L. Jenkins, Christianburg, VA (US); Robert C. Dilucclo, Haymarket, VA (US)

(73) Assignee: Actamax Surgical Materials, LLC, Berkeley, CA (US)

( * ) Notice: Subject to any disclaimer, the term of this patent is extended or adjusted under 35 U.S.C. 154(b) by 0 days.

(21) Appl. No.: 15/620,745

(22) Filed: Jun. 12, 2017

(65) Prior Publication Data

US 2017/0274117 A1    Sep. 28, 2017

Related U.S. Application Data

(63) Continuation of application No. 14/906,633, filed as application No. PCT/US2014/048459 on Jul. 28, 2014, now abandoned.

(60) Provisional application No. 61/859,458, filed on Jul. 29, 2013.

(51) Int. Cl.
    *A61K 31/77*    (2006.01)
    *A61L 24/04*    (2006.01)
    *A61L 24/00*    (2006.01)

(52) U.S. Cl.
    CPC ......... *A61L 24/046* (2013.01); *A61L 24/0031* (2013.01); *A61L 24/043* (2013.01); *A61L 2400/06* (2013.01)

(58) Field of Classification Search
    CPC .. A61L 24/043; A61L 24/0031; A61L 24/046; A61L 2400/06; C08L 5/02; C08L 71/02; A61K 31/77
    See application file for complete search history.

(56) References Cited

U.S. PATENT DOCUMENTS

| | | |
|---|---|---|
| 4,542,176 A | 9/1985 | Graham |
| 4,584,188 A | 4/1986 | Graham |
| 4,703,116 A | 10/1987 | Solarek et al. |
| 4,731,162 A | 3/1988 | Solarek et al. |
| 4,741,804 A | 5/1988 | Solarek et al. |
| 4,749,800 A | 6/1988 | Jobe et al. |
| 4,766,245 A | 8/1988 | Larkin et al. |
| 4,839,449 A | 6/1989 | Billmers et al. |
| 4,909,251 A | 3/1990 | Seelich |
| 4,911,926 A | 3/1990 | Henry et al. |
| 4,929,670 A | 5/1990 | Billmers et al. |
| 5,011,918 A | 4/1991 | Bilmers et al. |
| 5,049,634 A | 9/1991 | Tsai et al. |
| 5,092,883 A | 3/1992 | Eppley et al. |
| 5,116,824 A | 5/1992 | Miyata et al. |
| 5,162,430 A | 11/1992 | Rhee et al. |
| 5,196,441 A | 3/1993 | Kunisch et al. |
| 5,217,485 A | 6/1993 | Liu et al. |
| 5,275,838 A | 1/1994 | Merrill |
| 5,283,339 A | 2/1994 | Arnold et al. |
| 5,292,802 A | 3/1994 | Rhee et al. |
| 5,308,889 A | 5/1994 | Rhee et al. |
| 5,324,775 A | 6/1994 | Rhee et al. |
| 5,328,995 A | 7/1994 | Schaulin et al. |
| 5,451,398 A | 9/1995 | Vigh |
| 5,502,042 A | 3/1996 | Gruskin et al. |
| 5,505,952 A | 4/1996 | Jiang et al. |
| 5,514,379 A | 5/1996 | Weissleder et al. |
| 5,567,685 A | 10/1996 | Linden et al. |
| 5,643,575 A | 7/1997 | Martinez et al. |
| 5,733,563 A | 3/1998 | Fortier |
| 5,776,706 A | 7/1998 | Siiman et al. |
| 5,830,986 A | 11/1998 | Merrill et al. |
| 5,840,698 A | 11/1998 | Campbell et al. |
| 5,843,865 A | 12/1998 | Del Corral et al. |
| 5,874,500 A | 2/1999 | Rhee et al. |
| 5,990,237 A | 11/1999 | Bentley et al. |
| 6,051,648 A | 4/2000 | Rhee et al. |
| 6,121,375 A | 9/2000 | Eknoian |
| 6,150,472 A | 11/2000 | Engbers |
| 6,165,488 A | 12/2000 | Tardy et al. |
| 6,166,130 A | 12/2000 | Rhee et al. |
| 6,323,278 B2 | 11/2001 | Rhee et al. |
| 6,391,939 B2 | 5/2002 | Tayot et al. |
| 6,410,519 B1 | 6/2002 | Gruskin et al. |
| 6,458,147 B1 | 10/2002 | Cruise et al. |

(Continued)

FOREIGN PATENT DOCUMENTS

| | | |
|---|---|---|
| EP | 0961783 | 12/1999 |
| JP | 1982102932 | 6/1982 |

(Continued)

OTHER PUBLICATIONS

Ahmad, Shavej, et al., Dextran and 5-aminosalicylic Acid (5-ASA) Conjugates: Synthesis, Characterisation and Enzymic Hydrolysis, Carbohydrate Research, 2006, pp. 2694-2701, vol. 341.
Atassi, M.Z., Immunochemistry of Proteins, Plenum Press, New York, 1977, pp. 59-60, vol. 1.
Azzam, Tony, et al., Cationic Polysaccharides for Gene Delivery, Macromolecules, 2002, pp. 9947-9953, vol. 35, No. 27.
Balakrishnan, Biji, et al., Self-cross linking biopolymers as injectable in situ forming biodegradable scaffolds, Biomaterials, 2005, pp. 3941-3951, vol. 26.
Bruce, J. et al., Systematic Review of the Definition and Measurement of Anastomotic Leak after Gastrointestinal Surgery, British Journal of Surgery, 2001, pp. 1157-1168, vol. 88.
Basf Corp., Technical Bulletin, Pluronic F108 Block Copolymer Surfactant, 2004, 1 Page.

(Continued)

*Primary Examiner* — Ernst V Arnold
(74) *Attorney, Agent, or Firm* — Kevin M. Bull

(57) ABSTRACT

A hydrogel tissue adhesive formed by reacting an aldehyde-functionalized dextran containing pendant aldehyde groups with a multi-arm polyethylene glycol amine is described. The hydrogel exhibits little to no swell upon exposure to physiological conditions. The hydrogel may be useful as a tissue adhesive or sealant for medical applications that require a low swell hydrogel to inhibit complications, such as fibrosis, including scar formation or surgical adhesions.

21 Claims, No Drawings

(56) References Cited

U.S. PATENT DOCUMENTS

| | | |
|---|---|---|
| 6,458,889 B1 | 10/2002 | Trollsas et al. |
| 6,465,694 B1 | 10/2002 | Baudys et al. |
| 6,514,534 B1 | 2/2003 | Sawhney |
| 6,534,591 B2 | 3/2003 | Rhee et al. |
| 6,602,952 B1 | 8/2003 | Bentley et al. |
| 6,620,125 B1 | 9/2003 | Redl |
| 6,664,102 B2 | 12/2003 | Illman et al. |
| 6,689,399 B1 | 2/2004 | Dickson |
| 6,696,089 B2 | 2/2004 | Kabanov et al. |
| 6,703,047 B2 | 3/2004 | Sawhney et al. |
| 6,743,521 B2 | 6/2004 | Hubbell et al. |
| 6,756,518 B2 | 6/2004 | Gruskin et al. |
| 6,800,278 B1 | 10/2004 | Perrault et al. |
| 6,828,401 B2 | 12/2004 | Nho et al. |
| 6,833,408 B2 | 12/2004 | Sehl et al. |
| 6,844,028 B2 | 1/2005 | Mao et al. |
| 6,858,736 B2 | 2/2005 | Nho et al. |
| 6,896,725 B2 | 5/2005 | Thornton et al. |
| 6,949,524 B2 | 9/2005 | Singh et al. |
| 6,958,325 B2 | 10/2005 | Domb |
| 7,001,891 B1 | 2/2006 | Domb |
| 7,196,180 B2 | 3/2007 | Aeschlimann et al. |
| 7,217,845 B2 | 5/2007 | Rosen et al. |
| 7,255,999 B2 | 8/2007 | Singh et al. |
| 7,323,539 B2 | 1/2008 | Sunkara et al. |
| 7,347,850 B2 | 3/2008 | Sawhney |
| 7,459,185 B2 | 12/2008 | Gutowski et al. |
| 7,780,980 B2 | 8/2010 | Sawhney |
| 7,834,065 B2 | 11/2010 | Nakajima et al. |
| 7,837,986 B2 | 11/2010 | Chenault |
| 7,854,923 B2 | 12/2010 | Chen et al. |
| 7,868,132 B2 | 1/2011 | Chenault |
| 7,883,694 B2 | 2/2011 | Rhee et al. |
| 7,960,498 B2 | 6/2011 | Chenault et al. |
| 8,202,963 B2 | 6/2012 | Chenault et al. |
| 8,241,609 B2 | 8/2012 | Figuly et al. |
| 8,257,685 B2 | 9/2012 | Smyth et al. |
| 8,263,582 B2 | 9/2012 | Stergis et al. |
| 8,282,959 B2 | 10/2012 | Arthur et al. |
| 8,426,492 B2 | 4/2013 | Lu |
| 8,431,114 B2 | 4/2013 | Kodokian et al. |
| 8,466,327 B2 | 6/2013 | Arthur |
| 8,545,871 B2 | 10/2013 | Arthur et al. |
| 8,551,136 B2 | 10/2013 | Lu |
| 8,580,950 B2 | 11/2013 | Lu et al. |
| 8,580,951 B2 | 11/2013 | Lu et al. |
| 8,715,636 B2 | 5/2014 | Kodokian et al. |
| 8,778,326 B2 | 7/2014 | Lu et al. |
| 8,796,242 B2 | 8/2014 | Lu et al. |
| 8,951,989 B2 | 2/2015 | Wagman |
| 9,044,529 B2 | 6/2015 | Lu et al. |
| 2002/0146826 A1 | 10/2002 | Domb |
| 2002/0151520 A1 | 10/2002 | Gruskin |
| 2003/0022216 A1 | 1/2003 | Mao et al. |
| 2003/0027788 A1 | 2/2003 | Singh et al. |
| 2003/0064502 A1 | 4/2003 | Illman et al. |
| 2003/0087111 A1 | 5/2003 | Hubbell et al. |
| 2003/0108511 A1 | 6/2003 | Sawhney |
| 2003/0119985 A1 | 6/2003 | Sehl et al. |
| 2004/0086479 A1 | 5/2004 | Grinstaff et al. |
| 2004/0096507 A1 | 5/2004 | Kwang et al. |
| 2004/0225097 A1 | 11/2004 | Nho et al. |
| 2004/0235708 A1 | 11/2004 | Rhee et al. |
| 2005/0002893 A1 | 1/2005 | Goldmann |
| 2005/0020805 A1 | 1/2005 | Sunkara et al. |
| 2005/0288684 A1 | 12/2005 | Aronson et al. |
| 2006/0078536 A1 | 4/2006 | Kodokian et al. |
| 2006/0110427 A1 | 5/2006 | Molock et al. |
| 2006/0115531 A1 | 6/2006 | Chenault |
| 2006/0193899 A1 | 8/2006 | Sawhney |
| 2006/0292030 A1 | 12/2006 | Odermatt et al. |
| 2007/0031467 A1 | 2/2007 | Abrahams et al. |
| 2007/0048251 A1 | 3/2007 | Arthur |
| 2007/0249870 A1 | 10/2007 | Chenault |
| 2008/0004421 A1 | 1/2008 | Chenault et al. |
| 2008/0031824 A1 | 2/2008 | Smyth et al. |
| 2008/0051323 A1 | 2/2008 | Kosak |
| 2008/0220047 A1 | 9/2008 | Sawhney et al. |
| 2008/0319101 A1 | 12/2008 | Nakajima et al. |
| 2009/0035249 A1 | 2/2009 | Bhatia et al. |
| 2009/0054535 A1 | 2/2009 | Figuly et al. |
| 2010/0015231 A1 | 1/2010 | Lu |
| 2010/0016886 A1 | 1/2010 | Lu |
| 2010/0086678 A1 | 4/2010 | Arthur et al. |
| 2010/0112063 A1 | 5/2010 | Figuly et al. |
| 2010/0125155 A1 | 5/2010 | Arthur |
| 2010/0160960 A1 | 6/2010 | Wagman et al. |
| 2010/0255101 A1 | 10/2010 | Lu |
| 2010/0272804 A1 | 10/2010 | Lu |
| 2011/0224724 A1 | 9/2011 | Lu et al. |
| 2011/0250257 A1 | 10/2011 | Arthur et al. |
| 2011/0269916 A1 | 11/2011 | Chenault et al. |
| 2012/0004194 A1 | 1/2012 | Lu et al. |
| 2012/0035129 A1 | 2/2012 | Wagman |
| 2012/0094955 A1 | 4/2012 | Wagman |
| 2012/0148523 A1 | 6/2012 | Lu et al. |
| 2013/0035309 A1 | 2/2013 | Butterick et al. |

FOREIGN PATENT DOCUMENTS

| | | |
|---|---|---|
| JP | 198811167 | 1/1988 |
| WO | WO8700836 | 2/1987 |
| WO | WO9010441 | 9/1990 |
| WO | WO199115368 | 10/1991 |
| WO | WO9730103 | 8/1997 |
| WO | WO9901143 | 1/1999 |
| WO | WO0069925 | 11/2000 |
| WO | WO0149268 | 7/2001 |
| WO | WO0172280 | 10/2001 |
| WO | WO0187986 | 11/2001 |
| WO | WO02102864 | 12/2002 |
| WO | WO03020818 | 3/2003 |
| WO | WO03097759 | 11/2003 |
| WO | WO2006031358 | 3/2006 |
| WO | WO2006042161 | 4/2006 |
| WO | WO2006080523 | 8/2006 |
| WO | WO2006086510 | 8/2006 |
| WO | WO2008005207 | 1/2008 |
| WO | WO2008066787 | 6/2008 |
| WO | WO2009064977 | 5/2009 |
| WO | WO2010059279 | 5/2010 |
| WO | WO2010059280 | 5/2010 |
| WO | WO2010111570 | 9/2010 |
| WO | WO2010118284 | 10/2010 |

OTHER PUBLICATIONS

Buckmann, Andreas F, et al., Functionalization of Poly(ethylene glycol) and Monomethoxy-Poly(ethylene glycol), Makromolecular Chemistry, 1981, pp. 1379-1384, vol. 182.

Callant, Dominique et al., A New Approach to Dextran Derivatives with Pendent Aldehyde Groups, Reactive Polymers, 1988, p. 129-136., vol. 8.

Chen, Nicole, et al., Mechanisms of Aldehyde-Containing Paper Wet-Strength Resins, Industrial & Engineering Chemistry Research, 2002, pp. 5366-5371, vol. 41, No. 22.

Cortesi, Rita et al., Dextran Cross-linked Gelatin Microspheres as a Drug Delivery System, European Journal of Pharmaceutics and Biopharmaceutics, 1999, pp. 153-160., vol. 47.

Fishman, Alexander, et al., Synthesis and investigation of Novel Branched PEG-Based Soluble Polymer Supports, The Journal of Organic Chemistry, 2003, pp. 9843-9846, vol. 68.

Gill, Inderbir S., et al., Improved Hemostatis During Laparoscopic Partial Nephrectomy Using Gelatin Matrix Thrombin Sealant, Adult Urology, 2005, pp. 463-466, vol. 64, No. 3.

Greenwald, Richard B., et al., Drug Delivery Systems Employing 1.4-1.6-Elimination Poly(ethylene glycol) Prodrugs of Amine-Containing Compounds, Journal of Medicinal Chemistry, 1999, pp. 3657-3667, vol. 42, No. 18.

Halabi A. et al., Synthesis and Characterization of a Novel Dendritic Acrylic Monomer, The Journal of Organic Chemistry, 2000, pp. 9210-9213, vol. 65.

(56) References Cited

OTHER PUBLICATIONS

Harris, J. Milton, et al., Synthesis and Characterization of Poly(ethylene Glycol) Derivatives, Journal of Polymer Science: Polymer Chemistry Edition, 1984, pp. 341-352, vol. 22.

Harris, J. Milton, Laboratory Synthesis of Polyethylene Glycol Derivatives, JMS-Rev., Macromol, Chem, Phys, C 25 (3) 1985, pp. 325-373.

Harris, J. Milton, Synthesis of New Poly(Ethylene Glycol) Derivatives, PolyEthylene Glycol Chemistry: Biotechnical and Biomedical Applications, edited by Milton J. Harris, Plenum Press: New York, 1992, pp. 371-381.

Hofreiter, B.T., et al., Rapid Estimation of Dialdehyde Content of Periodate Oxystarch through Quanitative Alkaii Consumption, Analytical Chemistry, 1955, pp. 1930-1931, vol. 27, No. 12.

Hollander, Andreas, et al., Polymer Surface Chemistry for Biologically Active Materials, Applied Surface Science, 2004, pp. 145-150., vol. 235.

Kim, Jae Chan, et al., Evaluation of Tissue Adhesives in Closure of Scieral Tunnel Incisions, Journal of Cataract & Refractive Surgery, 1995, pp. 320-325, vol. 21.

Kurisawa, Motoichi, et al., Double-Stimuli-Responsive Degradation of Hydrogels Consisting of Oligopeptide-Terminated Poly(ethylene glycol) and Dextran with an Interpenetrating Polymer Network, Journal of Biomaterials Science Polymer Edition, 1997, pp. 691-708., vol. 8, No. 9.

Lara, V.S., et al., Dentin-induced in Vivo inflammatory Response and in Vitro Activation of Murine Macrophages, Journal of Dental Research, 2003, pp. 460-465, vol. 82, No. 6.

Merrill, Edward W., Poly(ethylene oxide) Star Molecules: Synthesis, Characterization, and Applications in Medicine and Biology, Journal of Biomaterials Science Polymer Edition, 1993, p. 1-11, vol. 5, No. ½.

Mo, Xiumei, et al., Soft Tissue Adhesive Composed of Modified Gelatin and Polysaccharides, Journal of Biomaterials Science Polymer Edition, 2000, pp. 341-351, vol. 11, No. 4.

Nagasaki, Yukio, et al., Formyl-Ended Heterobifunctional Poly(ethylene oxide): Synthesis of Poly(ethylene oxide) with a Formyl Group at One End and a Hydroxyl Group at the Other End, Bioconjugate Chemistry, 1995, pp. 231-233., vol. 6, No. 2.

Newkome, George R., Improved Synthesis of an Ethereal Tetraamine Core for Dendrimer Construction, The Journal of Organic Chemistry, 2002, pp. 3957-3960, vol. 67.

Pfannemuller, B. et al., Chemical Modification of the Surface of the Starch Granules, Starch/Starke, 1983, pp. 298-303., vol. 95, No. 9.

Rebizak, Richard et al., Macromolecular contrast agents for magnetic resonance imaging influence of polymer content in ligand on the paramagnetic properties, European Journal of Phamaceutical Sciences, 1999, pp. 243-248, vol. 7.

Sarayba. Melvin A., et al., Inflow of Ocular Surface Fluid Through clear Corneal Cataract incisions: A Laboratory Model, American Journal of Ophthalmology, Aug. 2004, pp. 206-210, vol. 138, No. 2.

Sgouras, D, et al., Method for the evaluation of biocompatibility of soluble synthetic polymers which have potential for biomedical use 1—Use of the tetrazolium-based colorimetric assay (MTT) as a preliminary screen for evaluation of in vitrocytotoxicity, Journal of Materials Sciences; Materials in Medicine, 1990, pp. 61-68., vol. 1.

Stone H. Harian, et al., Antibiotic Prophylaxis in Gatric, Biliary and Colonic Surgery, Ann .Surg., Oct. 1976, pp. 443-450.

Sweeney, Thomas, et al., Intestinal Anastomoses Detected with a Photopolymerized Hydrogel, Surgery, Feb. 2002, pp. 185-189., vol. 131, No. 2.

Thome, J. et al., Ultrathin Antibacterial Polyammonium Coatings on Polymer Surfaces, Surface and Coatings Technology, 2003, pp. 584-587, 174-175.

Yao, Zhong, et al., A Series of Novel Chitosan Derivatives; Synthesis, Characterization and Micellar Solubilization of Paclitaxel, Carbohydrate Polymers, 2007, pp. 781-792, vol. 68.

Zalipsky, Samuel, et al., Hydrazide Derivatives of Poly(ethylene glycol) and Their Bioconjugates, ACS Symposium Series; American Chemical Society, 1997, pp. 318-341.

Zalipsky, Samuel, et al., Preparation and Applications of Polyethylene Glycol-Polystyrene Graft Resin Supports for Solid-Phase Peptide Synthesis, Reactive Polymers, 1994, pp. 243-258, vol. 22.

Zhao, Huiru, et al., Determination of Degree of Substitution of Formyl Groups in Polyaidehyde Dextran by the Hydroxylamine Hydrochloride Method, Pharmaceutical Research, 1991, pp. 400-402., vol. 8, No. 3.

Zhao, Xuan, et al., Novel Degradable Poly(ethylene glycol) Esters for Drug Delivery, Poly(ethylene glycol) Chemistry and Biological Applications, Oxford University Press, 1998, pp. 458-472, Chapter 28.

LOW SWEEL TISSUE ADHESIVE AND SEALANT FORMULATIONS

CROSS-REFERENCE TO RELATED APPLICATIONS

This application is a continuation of U.S. application Ser. No. 14/906,633 filed Jan. 21, 2016, which is the US National Phase Application of International Application No. PCT/US2014/048459 filed Jul. 28, 2014, which designated the US and claims priority to U.S. Provisional Patent Application No. 61/859,458, filed Jul. 29, 2013, the entire contents of each of which are hereby incorporated by reference.

FIELD OF THE INVENTION

The present disclosure relates to the field of medical adhesives. More specifically, the present disclosure relates to a hydrogel tissue adhesive formed by reacting an aldehyde-functionalized dextran containing pendant aldehyde groups with a multi-arm polyethylene glycol amine.

BACKGROUND OF THE INVENTION

Tissue adhesives have many potential medical applications, including wound closure, supplementing or replacing sutures or staples in internal surgical procedures, preventing leakage of fluids such as blood, bile, gastrointestinal fluid and cerebrospinal fluid, adhesion of synthetic onlays or inlays to the cornea, drug delivery devices, and as anti-adhesion barriers to prevent post-surgical adhesions. Conventional tissue adhesives are generally not suitable for a wide range of adhesive applications. For example, cyanoacrylate-based adhesives have been used for topical wound closure, but the release of toxic degradation products limits their use for internal applications. Fibrin-based adhesives are slow curing, have poor mechanical strength, and pose a risk of viral infection. Additionally, fibrin-based adhesives do not bond covalently to the underlying tissue.

Several types of hydrogel tissue adhesives have been developed, which have improved adhesive and cohesive properties and are nontoxic (see, for example, Sehl et al., U.S. Patent Application Publication No. 2003/0119985, and Goldmann, U.S. Patent Application Publication No. 2005/0002893). These hydrogels are generally formed by reacting a component having nucleophilic groups with a component having electrophilic groups, which are capable of reacting with the nucleophilic groups of the first component, to form a crosslinked network via covalent bonding. However, these hydrogels typically swell, dissolve away too quickly, or lack sufficient adhesion or mechanical strength, thereby decreasing their effectiveness as surgical adhesives.

SUMMARY OF THE INVENTION

The present disclosure is directed to a hydrogel tissue adhesive and sealant that has good adhesion and cohesion properties, crosslinks readily at body temperature, does not degrade rapidly, is nontoxic to cells and non-inflammatory to tissue, and maintains dimensional stability better and longer than traditional oxidized polysaccharide-based hydrogel tissue adhesives.

In one embodiment, the present disclosure provides a kit for forming a low swell hydrogel comprising a first aqueous solution or dispersion comprising one or more aldehyde-functionalized dextrans containing pendant aldehyde groups, said aldehyde-functionalized dextrans having a weight-average molecular weight of about 10,000 to about 20,000 Daltons and an equivalent weight per aldehyde group of about 226 (degree of aldehyde substitution of about 90%) to about 170 (degree of aldehyde substitution of about 120%); and a second aqueous solution or dispersion comprising one or more polyethylene glycols having eight arms, substantially each arm of which is terminated with at least one primary amine group, wherein the polyethylene glycols have a number-average molecular weight of about 9,000 to about 11,000 Daltons; wherein (i) the total concentration of the aldehyde-functionalized dextrans containing pendant aldehyde groups in the first aqueous solution or dispersion is about 5 wt % to about 20 wt % and the total concentration of the polyethylene glycols in the second aqueous solution or dispersion is about 10 wt % to about 18 wt %; or (ii) the total concentration of the aldehyde-functionalized dextrans containing pendant aldehyde groups in the first aqueous solution or dispersion is about 5 wt % to about 10 wt % and the total concentration of the polyethylene glycols in the second aqueous solution or dispersion is about 10 wt % to about 20 wt %.

In another embodiment, the present disclosure provides a dried hydrogel formed by a process comprising the steps of combining in a solvent one or more aldehyde-functionalized dextrans containing pendant aldehyde groups, said aldehyde-functionalized dextrans having a weight-average molecular weight of about 10,000 to about 20,000 Daltons and an equivalent weight per aldehyde group of about 226 (degree of aldehyde substitution of about 90%) to about 170 (degree of aldehyde substitution of about 120%), and one or more polyethylene glycols having eight arms, substantially each arm of the which is terminated with at least one primary amine group, said polyethylene glycols having a number-average molecular weight of about 9,000 to about 11,000 Daltons, to form a low swell hydrogel; wherein (i) the total concentration of the aldehyde-functionalized dextrans containing pendant aldehyde groups in the solvent is about 5 wt % to about 20 wt % and the total concentration of the polyethylene glycols in the solvent is about 10 wt % to about 18 wt %; or (ii) the total concentration of the aldehyde-functionalized dextrans containing pendant aldehyde groups in the solvent is about 5 wt % to about 10 wt % and the total concentration of the polyethylene glycols in the solvent is about 10 wt % to about 20 wt %; and treating said hydrogel to remove at least a portion of said solvent to form the dried hydrogel.

In another embodiment, the present disclosure provides a composition comprising the reaction product of at least one aldehyde-functionalized dextran containing pendant aldehyde groups, wherein the aldehyde-functionalized dextran has a weight-average molecular weight of about 10,000 to about 20,000 Daltons and an equivalent weight per aldehyde group of about 226 (degree of aldehyde substitution of about 90%) to about 170 (degree of aldehyde substitution of about 120%), and at least one polyethylene glycol having eight arms, substantially each arm of which is terminated with at least one primary amine group, wherein the polyethylene glycol has a number-average molecular weight of about 9,000 to about 11,000 Daltons; wherein (i) the composition contains about 5 wt % to about 20 wt % of the aldehyde-functionalized dextran and about 10 wt % to about 18 wt % of the polyethylene glycol; or the composition contains about 5 wt % to about 10 wt % of the aldehyde-functionalized dextran and about 10 wt % to about 20 wt % of the polyethylene glycol.

In another embodiment, the present disclosure provides a crosslinked hydrogel composition comprising at least one aldehyde-functionalized dextran containing pendant aldehyde groups, wherein the aldehyde-functionalized dextran has a weight-average molecular weight of about 10,000 to about 20,000 Daltons and an equivalent weight per aldehyde group of about 226 (degree of aldehyde substitution of about 90%) to about 170 (degree of aldehyde substitution of about 120%), and at least one polyethylene glycol having eight arms, substantially each arm of which is terminated with at least one primary amine group, wherein the polyethylene glycol has a number-average molecular weight of about 9,000 to about 11,000 Daltons; wherein (i) the composition contains about 5 wt % to about 20 wt % of the aldehyde-functionalized dextran and about 10 wt % to about 18 wt % of the polyethylene glycol; or (ii) the composition contains about 5 wt % to about 10 wt % of the aldehyde-functionalized dextran and about 10 wt % to about 20 wt % of the polyethylene glycol; and wherein said aldehyde-functionalized dextran and said polyethylene glycol are crosslinked through covalent bonds formed between the pendant aldehyde groups of dextran and the primary amine groups of the polyethylene glycol.

Finally, in another embodiment, the present disclosure provides a method for applying a coating to an anatomical site on tissue of a living organism comprising the steps of applying to the site (a) aldehyde-functionalized dextrans containing pendant aldehyde groups, wherein the aldehyde-functionalized dextrans have a weight-average molecular weight of about 10,000 to about 20,000 Daltons and an equivalent weight per aldehyde group of about 226 (degree of aldehyde substitution of about 90%) to about 170 (degree of aldehyde substitution of about 120%); followed by (b) polyethylene glycols having eight arms, substantially each arm of which is terminated with at least one primary amine group, wherein the polyethylene glycols have a number-average molecular weight of about 9,000 to about 11,000 Daltons, or (b) followed by (a), or premixing (a) and (b) and applying the resulting mixture to the site before the resulting mixture completely cures; and wherein the weight percent ratio of aldehyde-functionalized dextrans to polyethylene glycols is about 2:1 to about 1:4.

DETAILED DESCRIPTION

The present disclosure is related to compositions (e.g., hydrogels) formed by reacting an aldehyde-functionalized dextran containing pendant aldehyde groups with a water-dispersible, multi-arm polyethylene glycol amine. The compositions may be useful as tissue adhesives or sealants for medical applications that require a tissue adhesive or sealant that exhibits little or no swell when exposed to physiological conditions.

As used above and throughout the description of the disclosure, the following terms, unless otherwise indicated, shall be defined as follows:

The term "aldehyde-functionalized dextran(s)" as used herein, refers to a dextran that has been chemically modified to introduce pendant aldehyde groups into the molecule. In many instances, the terms dextran and dextrans are used interchangeably. The pendant aldehyde groups may be single aldehyde groups or dialdehydes. As defined herein, aldehyde-functionalized dextran does not include dextran that is oxidized by cleavage of the dextran ring to introduce aldehyde groups. Oxidation of the dextran ring results in dialdehydes formed by opening the rings of dextran.

The term "pendant aldehyde group" refers to an aldehyde group that is attached to dextran via one of the ring hydroxyl groups.

The term "degree of aldehyde substitution" refers to the mole percent of pendant aldehyde groups per mole of repeat units, i.e., (moles of pendant aldehyde groups/moles of dextran repeat units)×100. The degree of aldehyde substitution is calculated as described in the Examples herein.

The term "equivalent weight per aldehyde group" refers to the molecular weight of dextran divided by the number of pendant aldehyde groups introduced into the molecule.

The term "multi-arm polyethylene glycol amine" refers to a polyethylene glycol (PEG) polymer having three or more polyethylene glycol chains ("arms"), which may be linear or branched, emanating from a central structure, which may be a single atom, a core molecule, or a polymer backbone, wherein at least three of the branches ("arms") are terminated by at least one primary amine group. The multi-arm polyethylene glycol amine is water soluble or is able to be dispersed in water to form a colloidal suspension capable of reacting with a second reactant in aqueous solution or dispersion.

The term "dispersion" as used herein, refers to a colloidal suspension capable of reacting with a second reactant in an aqueous medium.

The term "branched" refers to a polyethylene glycol polymer having one or more branch points ("arms"), including star, dendritic, comb, highly branched, and hyperbranched polyethylene glycol polymers. Branches radiate from one or more trifunctional or higher functional branch points.

The term "dendritic" refers to a highly branched polymer having a branching structure that repeats regularly with each successive generation of monomer radiating from a core molecule.

The term "comb polymer" refers to a branched polymer in which linear side-chains emanate from trifunctional branch points on a linear polymer backbone.

The term "star polymer" refers to a branched polymer in which linear side-chains emanate from a single atom or a core molecule having a point of symmetry.

The term "hyperbranched polymer" refers to a highly branched polymer which is more branched than "highly branched," with order approaching that of an imperfect dendrimer.

The term "highly branched polymer" refers to a branched polymer having many branch points, such that the distance between branch points is small relative to the total length of arms.

The term "primary amine" refers to a neutral amino group having two free hydrogens. The amino group may be bound to a primary, secondary or tertiary carbon.

The term "multi-functional amine" refers to a chemical compound comprising at least two functional groups, at least one of which is a primary amine group.

The term "crosslink" refers to a bond or chain of atoms attached between and linking two different polymer chains.

The term "crosslink density" is herein defined as the reciprocal of the average number of chain atoms between crosslink connection sites.

The term "% by weight", also referred to herein as "wt %", refers to the weight percent relative to the total weight of the solution or dispersion, unless otherwise specified.

The term "anatomical site" refers to any external or internal part of the body of humans or animals.

The term "tissue" refers to any biological tissue, both living and dead, in humans or animals.

The term "hydrogel" refers to a water-swellable polymeric matrix, consisting of a three-dimensional network of macromolecules held together by covalent crosslinks that can absorb a substantial amount of water to form an elastic gel.

The term "dried hydrogel" refers to a hydrogel that has been treated to remove at least a portion of the solvent contained therein. Preferably, substantially all of the solvent is removed from the hydrogel.

The term "low swell" refers to hydrogels which exhibit a % swell of less than about 10%, more particularly about 5%, more particularly about 2%, more particularly about 1%, and even more particularly about 0% as measured by the hydrolysis method described in the Examples. The method is an in-vivo model wherein swell is the percentage increase in the length of the hydrogel relative to its initial length. In some embodiments, the hydrogels exhibit a negative swell, i.e. the hydrogels shrink. The present disclosure also embodies these hydrogels exhibiting a negative swell.

The term "$M_w$" as used herein refers to the weight-average molecular weight.

The term "$M_n$" as used herein refers to the number-average molecular weight.

The term "$M_z$" as used herein refers to the z-average molecular weight.

The term "medical application" refers to medical applications as related to humans and animals.

The meaning of abbreviations used is as follows: "min" means minute(s), "h" means hour(s), "sec" means second(s), "d" means day(s), "mL" means milliliter(s), "L" means liter(s), "µL" means microliter(s), "cm" means centimeter(s), "mm" means millimeter(s), "µm" means micrometer(s), "mol" means mole(s), "mmol" means millimole(s), "g" means gram(s), "mg" means milligram(s), "mol %" means mole percent, "Vol" means volume, "w/w" means weight per weight, "Da" means Daltons, "kDa" means kiloDaltons, the designation "10K" means that a polymer molecule possesses a number-average molecular weight of 10 kiloDaltons, "M" means molarity, "kPa" means kilopascals, "psi" means pounds per square inch, "rpm" means revolutions per minute", "$^1$H NMR" means proton nuclear magnetic resonance spectroscopy, "13-C NMR" means carbon 13 nuclear magnetic resonance spectroscopy, "ppm" means parts per million, "cP" means centipoise, "PBS" means phosphate-buffered saline, "MWCO" means molecular weight cut off.

A reference to "Aldrich" or a reference to "Sigma" means the said chemical or ingredient was obtained from Sigma-Aldrich, St. Louis, Mo.

Aldehyde-Functionalized Dextran

Aldehyde-functionalized dextran suitable for use herein is dextran that has been chemically modified to introduce pendant aldehyde groups into the molecule. The pendant aldehyde groups may be single aldehyde groups or dialdehydes. The pendant aldehyde groups of the aldehyde-functionalized dextran disclosed herein are attached to dextran through linking groups. In one embodiment, the linking groups comprise carbon, hydrogen, and oxygen atoms, but do not contain a nitrogen atom. In one embodiment, the linking groups are attached to dextran by ether linkages. Aldehyde-functionalized dextran having these types of linking groups are more stable in aqueous solution than oxidized polysaccharides or aldehyde-functionalized polysaccharides having other types of linking groups, such as those that contain a nitrogen atom or are linked to the polysaccharide by other chemical linkages (e.g., amide or urethane). These more stable dextrans are, therefore, more practical for commercial purposes. In one embodiment, the linking groups are attached to dextran by ester linkages. The ester linkages may be used to provide a faster degrading hydrogel. In one embodiment, the linking group contains an alkoxy group alpha to the pendant aldehyde group (i.e., on an adjacent carbon atom). In another embodiment, the linking group does not contain an alkoxy group beta to the pendant aldehyde group (i.e., on the second carbon atom from the aldehyde group).

As used herein, aldehyde-functionalized dextran does not include dextran that is oxidized by cleavage of the dextran ring to introduce aldehyde groups. Oxidation of the dextran ring results in dialdehydes formed by opening the rings of dextran. Therefore, the dialdehyde groups formed by oxidation of dextran rings are not pendant aldehyde groups as defined herein.

Aldehyde-functionalized dextran may be prepared by chemically modifying dextran to introduce pendant aldehyde groups. Dextran is available commercially from sources such as Sigma Chemical Co. (St. Louis, Mo.). Typically, dextran is a heterogeneous mixture having a distribution of different molecular weights, and are characterized by an average molecular weight, for example, the weight-average molecular weight ($M_w$), or the number average molecular weight ($M_n$), as is known in the art. Therefore, the aldehyde-functionalized dextran prepared from these dextrans are also a heterogeneous mixture having a distribution of different molecular weights. Suitable aldehyde-functionalized dextran has a weight-average molecular weight of about 10,000 to about 20,000 Daltons, more particularly about 13,000 to about 17,000 Daltons, more particularly about 14,000 to about 16,000 Daltons, and more particularly about 15,000 Daltons. In one embodiment, the aldehyde-functionalized dextran has a weight-average molecular weight of about 15,000 Daltons.

Aldehyde-functionalized dextran may be prepared using methods known in the art. Aldehyde-functionalized dextran may be prepared using any of the methods described by Mehta et al. (WO 99/07744). For example, dextran may be reacted with allyl glycidyl ether in an acid aqueous medium to form allyloxy dextran which is then oxidized by ozonolysis to cleave the double bond and introduce a terminal aldehyde group, as described in detail in the Examples herein below. Additionally, glycidol may be reacted with a dextran in a basic aqueous medium to give an alkylated dextran, as described by Chen (*Biotechnology Techniques* 3:131-134, 1989). Periodate oxidation of the alkylated dextran yields an aldehyde-functionalized dextran having pendant aldehyde groups. The aldehyde-functionalized dextran may also be prepared by the method described by Solarek et al. (U.S. Pat. No. 4,703,116) wherein dextran is reacted with a derivatizing acetal reagent in the presence of base and then the acetal is hydrolyzed by adjusting the pH to less than 7.0.

Aldehyde-functionalized dextran having dialdehyde functional groups can be prepared by first attaching a pendant group containing either a terminal diene or by attaching a cyclic, disubstituted olefin to the dextran ring. Attachment of the pendant groups can be accomplished using a variety of methods, including reaction of dextran with glycidyl ethers containing cyclic olefins or terminal dienes, or reaction with carboxylic acids or derivatives thereof which also contain cyclic olefins or terminal dienes. Oxidation of dextran derivatized with cyclic olefins or terminal dienes using methods known in the art, such as ozonolysis, yield dextran derivatized with pendant dialdehydes.

The equivalent weight per aldehyde group and the degree of aldehyde substitution may be determined using methods known in the art, as described in detail in the Examples herein. Suitable aldehyde-functionalized dextran has an equivalent weight per aldehyde group of about 226 (degree of aldehyde substitution of about 90%) to about 170 (degree of aldehyde substitution of about 120%), more particularly about 226 (degree of aldehyde substitution of about 90%) to about 185 (degree of aldehyde substitution of about 110%), more particularly about 222 (degree of aldehyde substitution of about 92%) to about 189 (degree of aldehyde substitution of about 108%), more particularly about 219 (degree of aldehyde substitution of about 93%) to about 190 (degree of aldehyde substitution of about 107%), more particularly about 217 (degree of aldehyde substitution of about 94%) to about 192 (degree of aldehyde substitution of about 106%), more particularly about 212 (degree of aldehyde substitution of about 96%), to about 196 (degree of aldehyde substitution of about 104%), more particularly about 210 (degree of aldehyde substitution of about 97%), to about 190 (degree of aldehyde substitution of about 107%), more particularly about 204 (degree of aldehyde substitution of about 100%), to about 196 (degree of aldehyde substitution of about 104%), more particularly about 177 (degree of aldehyde substitution of about 115%). In one particular embodiment, the equivalent weight per aldehyde group is about 216 (degree of aldehyde substitution about 94%). It is to be understood that any aldehyde-functionalized dextran equivalent weight per aldehyde group within the range of about 226 (degree of aldehyde substitution of about 90%) to about 170 (degree of aldehyde substitution of about 120%) can be useful in the present disclosure.

Multi-Arm Polyethylene Glycol Amines

Suitable multi-arm polyethylene glycol amines include compounds having 3, 4, 6, or 8 arms terminated with primary amines (referred to herein as 3, 4, 6, or 8-arm star PEG amines, respectively). In one embodiment, the multi-arm polyethylene glycol amine is an 8-arm PEG amine.

Multi-arm polyethylene glycol amines may have a number-average molecular weight of about 9,000 to about 11,000 Daltons, more particularly from about 9,500 to about 10,500 Daltons, and more particularly about 10,000 Daltons. In one embodiment, the multi-arm polyethylene glycol amine is an 8-arm polyethylene glycol having eight arms terminated by a primary amine group and having a number-average molecular weight of about 10,000 Daltons.

The multi-arm polyethylene glycol amines are either available commercially or may be prepared using methods known in the art. For example, multi-arm polyethylene glycols, wherein substantially each arm is terminated by a primary amine group, may be prepared by putting amine ends on multi-arm polyethylene glycols (e.g., 3, 4, 6, and 8-arm star polyethylene glycols, available from companies such as Nektar Transforming Therapeutics; SunBio, Inc., Anyang City, South Korea; NOF Corp., Tokyo, Japan; or JenKem Technology USA, Allen, Tex.) using the method described by Buckmann et al. (*Makromol. Chem.* 182:1379-1384, 1981). In that method, the multi-arm polyethylene glycol is reacted with thionyl bromide to convert the hydroxyl groups to bromines, which are then converted to amines by reaction with ammonia at 100° C. Additionally, multi-arm polyethylene glycol amines may be prepared from multi-arm polyols using the method described by Chenault (commonly owned U.S. Pat. No. 7,868,132). In that method, the multi-arm polyether is reacted with thionyl chloride to convert the hydroxyl groups to chlorine groups, which are then converted to amines by reaction with aqueous or anhydrous ammonia. Other methods that may be used for preparing multi-arm polyethylene glycol amines are described by Merrill et al. in U.S. Pat. No. 5,830,986, and by Chang et al. in WO 97/30103.

In one embodiment, the multi-arm polyethylene glycol amine is an eight-arm branched end polyethylene glycol amine having two primary amine groups at the end of the polymer arms and having a number-average molecular weight of about 10,000 Daltons, as described by Arthur et al. (U.S. Pat. No. 8,282,959).

In another embodiment, the multi-arm polyethylene glycol amine is a mixture of an eight-arm branched end polyethylene glycol amine having two primary amine groups at the end of the polymer arms and having a number-average molecular weight of about 10,000 Daltons, and an eight-arm polyethylene glycol amine having eight arms terminated by a primary amine group and having a number-average molecular weight of about 10,000 Daltons.

It should be recognized that the water-dispersible, multi-arm polyethylene glycol amines are generally a somewhat heterogeneous mixture having a distribution of arm lengths and in some cases, a distribution of species with different numbers of arms. When a multi-arm amine has a distribution of species having different numbers of arms, it can be referred to based on the average number of arms in the distribution. For example, in one embodiment the multi-arm amine is an 8-arm star PEG amine, which comprises a mixture of multi-arm star PEG amines, some having less than and some having more than 8 arms; however, the multi-arm star PEG amines in the mixture have an average of 8 arms. Therefore, the terms "8-arm", "6-arm", "4-arm" and "3-arm" as used herein to refer to multi-arm amines, should be construed as referring to a heterogeneous mixture having a distribution of arm lengths and in some cases, a distribution of species with different numbers of arms, in which case the number of arms recited refers to the average number of arms in the mixture.

Methods of Using the Hydrogel Tissue Adhesive

The hydrogel tissue adhesive disclosed herein may be used in various forms. In one embodiment, the aldehyde-functionalized dextran containing pendant aldehyde groups and the multi-arm polyethylene glycol amine are used as components of aqueous solutions or dispersions. To prepare an aqueous solution or dispersion comprising an aldehyde-functionalized dextran (referred to herein as the "first aqueous solution or dispersion"), at least one aldehyde-functionalized dextran is added to water to give a concentration of about 5% to about 20%, more particularly from about 5% to about 15%, and more particularly from about 5% to about 10% by weight relative to the total weight of the solution or dispersion. Additionally, a mixture of at least two different aldehyde-functionalized dextrans having different weight-average molecular weights, different degrees of aldehyde substitution, or both different weight-average molecular weights and degrees of aldehyde substitution may be used. Where a mixture of aldehyde-functionalized polysaccharides is used, the total concentration of the aldehyde-functionalized polysaccharides is about 5% to about 20% by weight, more particularly from about 5% to about 15%, and more particularly from about 5% to about 10% by weight relative to the total weight of the solution or dispersion.

Similarly, to prepare an aqueous solution or dispersion comprising a multi-arm polyethylene glycol amine (referred to herein as the "second aqueous solution or dispersion"), at least one water-dispersible, multi-arm polyethylene glycol amine (e.g., 8-arm PEG amine) is added to water to give a concentration of about 10% to about 20% by weight, more particularly from about 10% to about 18% by weight relative to the total weight of the solution or dispersion. The optimal concentration to be used depends on the intended application and on the concentration of the aldehyde-functionalized dextran used in the first aqueous solution or dispersion. Additionally, a mixture of different multi-arm polyethylene glycol amine having different number-average molecular weights, different numbers of arms, or both different number-average molecular weights and different numbers of arms may be used. Where a mixture of multi-arm polyethylene glycol amine is used, the total concentration of the multi-arm amines is about 10% to about 20% by weight, more particularly from about 10% to about 18% by weight relative to the total weight of the solution or dispersion.

For use on living tissue, it is preferred that the first aqueous solution or dispersion and the second aqueous solution or dispersion be sterilized to prevent infection. Any suitable sterilization method known in the art that does not adversely affect the ability of the components to react to form an effective hydrogel may be used, including, but not limited to, electron beam irradiation, gamma irradiation, ethylene oxide sterilization, or filtration through a 0.2 µm pore membrane.

The first aqueous solution or dispersion and the second aqueous solution or dispersion may further comprise various additives depending on the intended application. Preferably, the additive does not interfere with effective gelation to form a hydrogel. The amount of the additive used depends on the particular application and may be readily determined by one skilled in the art using routine experimentation. For example, the first aqueous solution or dispersion and/or the second aqueous solution or dispersion may comprise at least one additive selected from pH modifiers, antimicrobials, colorants, surfactants, pharmaceutical drugs and therapeutic agents.

The first aqueous solution or dispersion and/or the second aqueous solution or dispersion may optionally include at least one pH modifier to adjust the pH of the solution(s) or dispersion(s). Suitable pH modifiers are well known in the art. The pH modifier may be an acidic or basic compound. Examples of acidic pH modifiers include, but are not limited to, carboxylic acids, inorganic acids, and sulfonic acids. Examples of basic pH modifiers include, but are not limited to, hydroxides, alkoxides, nitrogen-containing compounds other than primary and secondary amines, and basic carbonates and phosphates.

The first aqueous solution or dispersion and/or the second aqueous solution or dispersion may optionally include at least one antimicrobial agent. Suitable antimicrobial preservatives are well known in the art. Examples of suitable antimicrobials include, but are not limited to, alkyl parabens, such as methylparaben, ethylparaben, propylparaben, and butylparaben; triclosan; chlorhexidine; cresol; chlorocresol; hydroquinone; sodium benzoate; and potassium benzoate.

The first aqueous solution or dispersion and/or the second aqueous solution or dispersion may optionally include at least one colorant to enhance the visibility of the solution(s) or dispersion(s). Suitable colorants include dyes, pigments, and natural coloring agents. Examples of suitable colorants include, but are not limited to, FD&C and D&C colorants, such as FD&C Violet No. 2, FD&C Blue No. 1, D&C Green No. 6, D&C Green No. 5, D&C Violet No. 2; and natural colorants such as beetroot red, canthaxanthin, chlorophyll, eosin, saffron, and carmine.

The first aqueous solution or dispersion and/or the second aqueous solution or dispersion may optionally include at least one surfactant. Surfactant, as used herein, refers to a compound that lowers the surface tension of water. The surfactant may be an ionic surfactant, such as sodium lauryl sulfate, or a neutral surfactant, such as polyoxyethylene ethers, polyoxyethylene esters, and polyoxyethylene sorbitan.

Additionally, the first aqueous solution or dispersion and/or the second aqueous solution or dispersion may optionally include at least one pharmaceutical drug or therapeutic agent. Suitable drugs and therapeutic agents are well known in the art (for example see the United States Pharmacopeia (USP), Physician's Desk Reference (Thomson Publishing), The Merck Manual of Diagnosis and Therapy 18th ed., Mark H. Beers and Robert Berkow (eds.), Merck Publishing Group, 2006; or, in the case of animals, The Merck Veterinary Manual, 9th ed., Kahn, C. A. (ed.), Merck Publishing Group, 2005). Nonlimiting examples include anti-inflammatory agents, for example, glucocorticoids such as prednisone, dexamethasone, budesonide; non-steroidal anti-inflammatory agents such as indomethacin, salicylic acid acetate, ibuprofen, sulindac, piroxicam, and naproxen; fibrinolytic agents such as a tissue plasminogen activator and streptokinase; anti-coagulants such as heparin, hirudin, ancrod, dicumarol, sincumar, iloprost, L-arginine, dipyramidole and other platelet function inhibitors; antibodies; nucleic acids; peptides; hormones; growth factors; cytokines; chemokines; clotting factors; endogenous clotting inhibitors; antibacterial agents; antiviral agents; antifungal agents; anti-cancer agents; cell adhesion inhibitors; healing promoters; vaccines; thrombogenic agents, such as thrombin, fibrinogen, homocysteine, and estramustine; radio-opaque compounds, such as barium sulfate and gold particles and radiolabels.

Additionally, the second aqueous solution or dispersion comprising the multi-arm polyethylene glycol amine may optionally comprise at least one other multi-functional amine having one or more primary amine groups to provide other beneficial properties, such as hydrophobicity or modified crosslink density. The multi-functional amine is capable of inducing gelation when mixed with an oxidized dextran in an aqueous solution or dispersion. The multi-functional amine may be a second multi-arm polyethylene glycol amine, such as those described above, or another type of multi-functional amine, including, but not limited to, linear and branched diamines, such as diaminoalkanes, polyaminoalkanes, and spermine; branched polyamines, such as polyethylenimine; cyclic diamines, such as N, N'-bis(3-aminopropyl)piperazine, 5-amino-1,3,3-trimethylcyclohexanemethylamine, 1,3-bis(aminomethyl)cyclohexane, 1, 4-diaminocyclohexane, and p-xylylenediamine; aminoalkyltrialkoxysilanes, such as 3-aminopropyltrimethoxysilane and 3-aminopropyltriethoxysilane; am inoalkyldialkoxyalkylsilanes, such as 3-aminopropyldiethoxymethylsilane, dihydrazides, such as adipic dihydrazide; linear polymeric diamines, such as linear polyethylenimine, α,ω-amino-terminated polyethers, α,ω-bis(3-aminopropyl)polybutanediol, β,ω-1-amino-terminated polyethers (linear Jeffamines®); comb polyamines, such as chitosan, polyallylamine, and polylysine, and di- and polyhydrazides, such as bis(carboxyhydrazido)polyethers and poly(carboxyhydrazido) star polyethers. Many of these compounds are commercially available from companies such as Sigma-Aldrich and Huntsman LLC. Typically, if present, the multi-functional amine is used at a concentration of about 5% by weight to about 1000% by weight relative to the weight of the multi-arm polyethylene glycol amine in the aqueous solution or dispersion.

When the first aqueous solution or dispersion and the second aqueous solution or dispersion are mixed they react to form a crosslinked hydrogel composition comprising at least one aldehyde-functionalized dextran containing pendant aldehyde groups; and at least one multi-arm polyethylene glycol amine wherein substantially each arm of which is terminated with at least one primary amine group, and wherein the aldehyde-functionalized dextran and the multi-arm polyethylene glycol amine are crosslinked through covalent bonds formed between the pendant aldehyde groups of the aldehyde-functionalized dextran and the primary amine groups of the multi-arm polyethylene glycol amine. The covalent bonds may be imine, aminal or hemi-aminal bonds.

In one embodiment, the present disclosure relates to a composition comprising the reaction product of at least one aldehyde-functionalized dextran containing pendant aldehyde groups, wherein the aldehyde-functionalized dextran has a weight-average molecular weight of about 10,000 to about 20,000 Daltons and an equivalent weight per aldehyde group of about 226 (a degree of aldehyde substitution of about 90%) to about 170 (a degree of aldehyde substitution of about 120%), and at least one polyethylene glycol having eight arms, substantially each arm of which is terminated with at least one primary amine group, wherein the polyethylene glycol has a number-average molecular weight of about 9,000 to about 11,000 Daltons; wherein (i) the composition contains about 5 wt % to about 20 wt % of the aldehyde-functionalized dextran and about 10 wt % to about 18 wt % of the polyethylene glycol; or (ii) the composition contains about 5 wt % to about 10 wt % of the aldehyde-functionalized dextran and about 10 wt % to about 20 wt % of the polyethylene glycol.

In another embodiment, the present disclosure relates to a crosslinked hydrogel composition comprising at least one aldehyde-functionalized dextran containing pendant aldehyde groups, wherein the aldehyde-functionalized dextran has a weight-average molecular weight of about 10,000 to about 20,000 Daltons and an equivalent weight per aldehyde group of about 226 (a degree of aldehyde substitution of about 90%) to about 170 (a degree of aldehyde substitution of about 120%), and at least one polyethylene glycol having eight arms, substantially each arm of which is terminated with at least one primary amine group, wherein the polyethylene glycol has a number-average molecular weight of about 9,000 to about 11,000 Daltons, wherein (i) the composition contains about 5 wt % to about 20 wt % of the aldehyde-functionalized dextran and about 10 wt % to about 18 wt % of the polyethylene glycol; or (ii) the composition contains about 5 wt % to about 10 wt % of the aldehyde-functionalized dextran and about 10 wt % to about 20 wt % of the polyethylene glycol; and wherein said aldehyde-functionalized dextran and said polyethylene glycol are crosslinked through covalent bonds formed between the pendant aldehyde groups of dextran and the primary amine groups of the polyethylene glycol.

The swelling of the hydrogel may be substantially reduced or eliminated by using the prescribed amounts of the aldehyde-functionalized dextran in the first aqueous solution or dispersion and the multi-arm polyethylene amine in the second aqueous solution or dispersion in terms of weight percent and/or by altering the amount of functionalization of either component, as shown in the Examples herein below.

The first aqueous solution or dispersion and the second aqueous solution or dispersion may be used to apply a coating to an anatomical site on tissue of a living organism. The two aqueous solutions or dispersions may be applied to the site in any number of ways. Once both solutions or dispersions are combined on a site, they crosslink to form a hydrogel which provides either a coating on the site, a barrier film, a filler/spacer or a sealant.

In one embodiment, the two aqueous solutions or dispersions are applied to the site sequentially using any suitable means including, but not limited to, spraying, brushing with a cotton swab or brush, or extrusion using a pipette, or a syringe. The solutions or dispersions may be applied in any order. Then, the solutions or dispersions are mixed on the site using any suitable device, such as a cotton swab, a spatula, or the tip of the pipette or syringe.

In another embodiment, the two aqueous solutions or dispersions are mixed manually before application to the site. The resulting mixture is then applied to the site before it completely cures using a suitable applicator, as described above.

In one embodiment, the present disclosure relates to a method for applying a low swell coating to an anatomical site on tissue of a living organism comprising the steps of applying to the site (a) aldehyde-functionalized dextrans containing pendant aldehyde groups, wherein the aldehyde-functionalized dextrans have a weight-average molecular weight of about 10,000 to about 20,000 Daltons and an equivalent weight per aldehyde group of about 226 (a degree of aldehyde substitution of about 90%) to about 170 (a degree of aldehyde substitution of about 120%); followed by polyethylene glycols having eight arms, substantially each arm of which is terminated with at least one primary amine group, wherein the polyethylene glycols have a number-average molecular weight of about 9,000 to about 11,000 Daltons. Alternatively, the method for applying the coating may be reversed such that the polyethylene glycols are applied first followed by the aldehyde-functionalized dextrans. The aldehyde-functionalized dextrans and the polyethylene glycols may also be premixing to form a mixture and then the resulting mixture is applied to the site before it completely cures.

The relative amounts of the aldehyde-functionalized dextrans and the polyethylene glycols applied may be between about 2:1 (i.e. 20 wt % dextran to 5 wt % PEG) to about 1:4 (i.e. 5 wt % dextran to 20 wt % PEG). More particularly, the relative amounts of the aldehyde-functionalized dextrans and the polyethylene glycols applied may be between about 2:1 (i.e. 20 wt % dextran to 10 wt % PEG) to about 5:18 (i.e. 5 wt % dextran to 18 wt % PEG). Even more particularly, the relative amounts of the aldehyde-functionalized dextrans and the polyethylene glycols applied may be between about 1:1 (i.e. 10 wt % dextran to 10 wt % PEG) to about 1:4 (i.e. 5 wt % dextran to 20 wt % PEG). Even more particularly, the relative amounts of the aldehyde-functionalized dextrans and the polyethylene glycols applied may be between about 1:1 (i.e. 10 wt % dextran to 10 wt % PEG) to about 5:18 (i.e. 5 wt % dextran to 18 wt % PEG).

For example, the method for applying a low swell coating to an anatomical site on tissue of a living organism may include the steps of applying to the site (a) aldehyde-functionalized dextrans containing pendant aldehyde groups, wherein the aldehyde-functionalized dextrans have a weight-average molecular weight of about 15,000 Daltons and an equivalent weight per aldehyde group of about 177 (a degree of aldehyde substitution of about 115%); followed by polyethylene glycols having eight arms, substantially each arm of which is terminated with at least one primary amine group, wherein the polyethylene glycols have a number-average molecular weight of about 10,000 Daltons, wherein the weight percent ratio of aldehyde-functionalized dextrans to polyethylene glycols is about 1:1.5.

In another example, the method for applying a low swell coating to an anatomical site on tissue of a living organism may include the steps of applying to the site (a) aldehyde-functionalized dextrans containing pendant aldehyde groups, wherein the aldehyde-functionalized dextrans have a weight-average molecular weight of about 15,000 Daltons and an equivalent weight per aldehyde group of about 177 (a degree of aldehyde substitution of about 115%); followed by polyethylene glycols having eight arms, substantially each arm of which is terminated with at least one primary amine group, wherein the polyethylene glycols have a number-average molecular weight of about 10,000 Daltons, wherein the weight percent ratio of aldehyde-functionalized dextrans to polyethylene glycols is about 1:1.

The first aqueous solution or dispersion and the second aqueous solution or dispersion may be applied to the site simultaneously where they mix to form a hydrogel. For example, the two aqueous solutions or dispersions may be contained in separate barrels of a double-barrel syringe. In this way the two aqueous solutions or dispersions are applied simultaneously to the site with the syringe. Suitable double-barrel syringe applicators are known in the art. For example, Redl describes several suitable applicators for use in the invention in U.S. Pat. No. 6,620,125, (particularly FIGS. 1, 5, and 6, which are described in Columns 4, line 10 through column 6, line 47). The two aqueous solutions or dispersions may also be applied to the site using a dual-lumen catheter, such as those available from Bistech, Inc. (Woburn, Mass.). Additionally, injection devices for introducing two liquid components endoscopically into the body simultaneously are known in the art and may be adapted for the delivery of the two aqueous solutions or dispersions disclosed herein (see for example, Linder et al., U.S. Pat. No. 5,322,510).

In another embodiment, the first aqueous solution or dispersion and the second aqueous solution or dispersion may be premixed and delivered to the site using a double barrel syringe containing a motionless mixer, such as that available from ConProtec, Inc. (Salem, N.H.) or Mixpac Systems AG (Rotkreuz, Switzerland). Other suitable mixers are described by Ashmead et al. (U.S. Pat. Nos. 8,246,241 and 8,277,113; and U.S. Patent Application Publication Nos. 2012/0325854 and 2013/0020352). Alternatively, the mixing tip may be equipped with a spray head, such as that described by Cruise et al. in U.S. Pat. No. 6,458,147. Additionally, the mixture of the two aqueous solutions or dispersions from the double-barrel syringe may be applied to the site using a catheter or endoscope. Devices for mixing a two liquid component tissue adhesive and delivering the resulting mixture endoscopically are known in the art and may be adapted for the mixing and delivery of the two aqueous solutions or dispersions disclosed herein (see for example, Nielson, U.S. Pat. No. 6,723,067; and Redl et al., U.S. Pat. No. 4,631,055).

In another embodiment, the two aqueous solutions or dispersions may be applied to the site using a spray device, such as those described by Fukunaga et al. (U.S. Pat. No. 5,582,596), Delmotte et al. (U.S. Pat. No. 5,989,215) or Sawhney (U.S. Pat. No. 6,179,862) or Brunk et al. (U.S. Patent Application Publication Nos. 2012/0000935 and 2012/0000993).

In another embodiment, the two aqueous solutions or dispersions may be applied to the site using a minimally invasive surgical applicator, such as those described by Sawhney (U.S. Pat. No. 7,347,850).

In another embodiment, the hydrogel tissue adhesive disclosed herein may be used in the form of a dried hydrogel. In this embodiment, a dried hydrogel is prepared by combining in a solvent at least one aldehyde-functionalized dextran with at least one multi-arm polyethylene glycol amine to form a hydrogel, and treating the hydrogel to remove at least a portion of the solvent to form the dried hydrogel. Suitable solvents include, but are not limited to, water, ethanol, isopropanol, tetrahydrofuran, hexanes, polyethylene glycol, and mixtures thereof. If two different solvents are used, the two solvents are miscible with each other. In one embodiment the solvent is water. The aldehyde-functionalized dextran and multi-arm polyethylene glycol amine may be combined in various ways. For example, the first aqueous solution or dispersion comprising the aldehyde-functionalized dextran and the second aqueous solution or dispersion comprising the multi-arm polyethylene glycol amine, may be prepared and mixed as described above to form the hydrogel. The solutions or dispersions used to prepare the hydrogel may further comprise various additives depending on the intended application. Any of the additives described above may be used. The hydrogel is then treated to remove at least a portion of the solvent contained therein to form the dried hydrogel. Preferably, substantially all of the solvent is removed from the hydrogel. The solvent may be removed from the hydrogel using methods known in the art, for example, using heat, vacuum, a combination of heat and vacuum, or flowing a stream of dry air or a dry inert gas such as nitrogen over the hydrogel. The dried hydrogel may be sterilized using the methods described above. The dried hydrogel may be applied to an anatomical site in a number of ways, as described below. The dried hydrogel may be hydrated on the site by the addition of a suitable aqueous solution such as water or a buffer (e.g., phosphate-buffered saline) or by the physiological fluids present at the site.

In one embodiment, the present disclosure relates to a dried hydrogel formed by a process comprising the steps of combining in a solvent one or more aldehyde-functionalized dextrans containing pendant aldehyde groups, said aldehyde-functionalized dextrans having a weight-average molecular weight of about 10,000 to about 20,000 Daltons and an equivalent weight per aldehyde group of about 226 (a degree of aldehyde substitution of about 90%) to about 170 (a degree of aldehyde substitution of about 120%), and one or more polyethylene glycols having eight arms, substantially each arm of the which is terminated with at least one primary amine group, said polyethylene glycols having a number-average molecular weight of about 9,000 to about 11,000 Daltons, to form a hydrogel, wherein (i) the total concentration of the aldehyde-functionalized dextrans containing pendant aldehyde groups in the solvent is about 5 wt % to about 20 wt % and the total concentration of the polyethylene glycols in the solvent is about 10 wt % to about 18 wt %; or (ii) the total concentration of the aldehyde-functionalized dextrans containing pendant aldehyde groups in the solvent is about 5 wt % to about 10 wt % and the total concentration of the polyethylene glycols in the solvent is about 10 wt % to about 20 wt %; and treating said hydrogel to remove at least a portion of said solvent to form the dried hydrogel.

In one embodiment, the dried hydrogel may be used in the form of a film. The dried hydrogel film may be formed by casting a mixture of the solutions or dispersions, as described above, on a suitable substrate and treating the resulting hydrogel to form a dried hydrogel film. The dried hydrogel film may be applied directly to an anatomical site. Additionally, the dried hydrogel film may be used to bond two anatomical sites together.

In another embodiment, the dried hydrogel may be used in the form of finely divided particles. The dried hydrogel particles may be formed by comminuting the dried hydrogel using methods known in the art, including, but not limited to, grinding, milling, or crushing with a mortar and pestle. The dried hydrogel particles may be applied to an anatomical site in a variety of ways, such as sprinkling or spraying, and may also be used to bond two anatomical sites together.

Kits

In one embodiment, the present invention relates to a kit for forming a low swell hydrogel including a first aqueous solution comprising one or more aldehyde-functionalized dextrans containing pendant aldehyde groups, said aldehyde-functionalized dextrans having a weight-average molecular weight of about 10,000 to about 20,000 Daltons and an equivalent weight per aldehyde group of about 226 (a degree of aldehyde substitution of about 90%) to about 170 (a degree of aldehyde substitution of about 120%), more particularly about 226 (a degree of aldehyde substitution of about 90%) to about 185 (a degree of aldehyde substitution of about 110%); and a second aqueous solution comprising one or more polyethylene glycols having eight arms, substantially each arm of which is terminated with at least one primary amine group, wherein the polyethylene glycols have a number-average molecular weight of about 9,000 to about 11,000 Daltons; wherein (i) the total concentration of the aldehyde-functionalized dextrans containing pendant aldehyde groups in the first aqueous solution is about 5 wt % to about 20 wt % and the total concentration of the polyethylene glycols in the second aqueous solution is about 10 wt % to about 18 wt %; or (ii) the total concentration of the aldehyde-functionalized dextrans containing pendant aldehyde groups in the first aqueous solution is about 5 wt % to about 10 wt % and the total concentration of the polyethylene glycols in the second aqueous solution is about 10 wt % to about 20 wt %. Each of the aqueous solutions or dispersions may be contained in any suitable vessel, such as a vial or a syringe barrel.

The total concentration of the aldehyde-functionalized dextrans containing pendant aldehyde groups in the first aqueous solution may also be about 5 wt % to about 10 wt % and the total concentration of the polyethylene glycols in the second aqueous solution may also be about 10 wt % to about 18 wt %.

For example, the kit for forming a low swell hydrogel may include a first aqueous solution comprising one or more aldehyde-functionalized dextrans containing pendant aldehyde groups, said aldehyde-functionalized dextrans having a weight-average molecular weight of about 15,000 Daltons and an equivalent weight per aldehyde group of about 177 (a degree of aldehyde substitution of about 115%); and a second aqueous solution comprising one or more polyethylene glycols having eight arms, substantially each arm of which is terminated with at least one primary amine group, wherein the polyethylene glycols have a number-average molecular weight of about 10,000 Daltons; wherein the total concentration of the aldehyde-functionalized dextrans containing pendant aldehyde groups in the first aqueous solution is about 10 wt % and the total concentration of the polyethylene glycols in the second aqueous solution is about 15 wt %.

In another example, the kit for forming a low swell hydrogel may include a first aqueous solution comprising one or more aldehyde-functionalized dextrans containing pendant aldehyde groups, said aldehyde-functionalized dextrans having a weight-average molecular weight of about 15,000 Daltons and an equivalent weight per aldehyde group of about 177 (a degree of aldehyde substitution of about 115%); and a second aqueous solution comprising one or more polyethylene glycols having eight arms, substantially each arm of which is terminated with at least one primary amine group, wherein the polyethylene glycols have a number-average molecular weight of about 10,000 Daltons; wherein the total concentration of the aldehyde-functionalized dextrans containing pendant aldehyde groups in the first aqueous solution is about 15 wt % and the total concentration of the polyethylene glycols in the second aqueous solution is about 15 wt %.

The kit may also include at least one aldehyde-functionalized dextran containing pendant aldehyde groups and at least one multi-arm polyethylene glycol amine in the form of finely divided powders, as described above. The powders may be contained in separate containers or they may be premixed and contained in a single container. The kit may also comprise an aqueous solution for hydrating the powders.

In another embodiment, the kit comprises a dried hydrogel as described above. The dried hydrogel may be in the form of a film, finely divided particles, or other dried forms. The kit may further comprise an aqueous solution for hydrating the dried hydrogel. The dried hydrogel particles may be contained in any suitable container.

Medical Applications

The hydrogel disclosed herein may be useful as a tissue adhesive or sealant for medical applications that require a tissue adhesive or sealant that exhibits little or no swell (e.g., low swell) when exposed to physiological conditions. In these applications, the aldehyde-functionalized dextran and the multi-arm polyethylene glycol amine combination (e.g., hydrogel, composition, or dried hydrogel) may be applied to the desired anatomical site using the methods described above.

In one embodiment, the present disclosure is directed to compositions having low swelling biocompatible polymers and methods using such compositions to inhibit fibrosis, including scar formation and surgical adhesions. The methods of the present disclosure include applying the aldehyde-functionalized dextran and the multi-arm polyethylene glycol amine combination to tissue involved in or affected by a surgical procedure wherein fibrosis, including scar formation, keloid formation and surgical adhesions, may occur.

Surgical adhesions, which include the attachment of organs or tissues to each other through scar tissue, can produce clinical problems. The formation of scar tissue is well known in surgical procedures or other tissue injuries and is required for proper wound healing. There are some cases wherein the scar tissue overgrows the intended region and creates surgical adhesions. These scar tissue surgical adhesions restrict the normal mobility and function of affected body parts. Where peripheral nerves are involved, fibrous adhesions may even elicit severe pain during normal movement.

For example, the formation of fibrous adhesions to the spinal cord dura which occurs as part of the natural healing process after laminectomy surgery is commonly occurring problem which causes poor surgical outcomes, persistent pain to patient and often requires a second surgery. The aldehyde-functionalized dextran and the multi-arm polyethylene glycol amine hydrogel of the present disclosure is an effective treatment or preventative measure in this surgical indication. The hydrogel provides low to zero swell at the application site to reduce or eliminate any increased pressure on the spinal cord. The hydrogel persists at the application site for a sufficient time to protect the dura from adhesion formation during normal soft tissue healing (e.g., 7-10 days). The hydrogel is biodegradable and dissolves within weeks or months after application, depending on the individual composition of the hydrogel. The hydrogel contains monomer and/or crosslinking units which are hydrolysable under physiological conditions, and are broken in the human or animal body.

A clinically important example of detrimental scar formation occurs with peridural fibrosis. This condition leads to recurrent low back pain and leg pain which can persist after lumbar laminectomy, laminotomy and discectomy. In this situation, scar formation restricts nerve root mobility and has been associated with recurrent pain in the same area that was treated.

A number of studies have been done to test various treatments for preventing peridural fibrosis. For example, fat grafts have been used with some success to prevent or ameliorate scar formation (e.g., spinal adhesion prevention). Gelfoam (denatured collagen gel) and silastic membranes have also showed some effectiveness in preventing adhesions. Later studies, however, indicated that Gelfoam was ineffective or promoted scar formation. Sodium hyaluronate is known to retard fibrosis and reduced fibroblast invasion in dog models. Another related product is DuraSeal Xact (Covidien) which is a synthetic resorbable hydrogel that was developed for use as a dural sealant to provide watertight closure and to also allow for inhibition of peridural fibrosis. Another product is Oxiplex/SP Gel (FzioMed) which is a combination of carboxymethyl cellulose and polyethylene oxide used to coat exposed surgical sites to prevent scarring.

The compositions and methods of the present disclosure are suitable for treating animals, preferably mammals, and more preferably humans. For example, a therapeutically effective amount of the low swell hydrogel, or related composition, as disclosed herein can be safely administered to treat a lesion in an animal to inhibit scar formation, and fibrosis in general.

In one embodiment, the compositions and methods of the present disclosure address a need in spinal surgery by providing a low swell, degradable material which allows for healing and also prevention of the formation of fibrous adhesions during the healing process. Adhesion compromise the success of spinal decompression surgeries by causing additional and sustainable pain and not allowing a reduction in pain to occur after the procedure.

The compositions and methods of the present disclosure are useful, for one or more of the reasons addressed herein, in the following procedures.

Spinal surgeries, including lumbar laminectomy, lumbar discectomy, flexor tendon surgery, spinal fusion and joint replacement or repair. In one embodiment, the present disclosure provides materials and methods for inhibiting fibrosis following laminectomy, in particular, inhibiting epidural (peridural) fibrosis following a lumbar laminectomy. For example, when applied to the site of the laminectomy the site may show reduced or minimal scar tissue formation and bone growth, and the dura mater may be visible as a smooth transparent membrane.

Abdominal procedures, including surgeries of the intestines, appendix, cholecystectomy, hernial repair, lysis of peritoneal adhesions, kidney, bladder, urethra, and prostate.

Gynecological procedures, including surgeries to treat infertility due to bilateral tubal disease with adhesion attached to ovaries, fallopian tubes and fimbriae, salingostomy, salpingolysis and ovariolysis. These procedures include other gynecological surgeries, such as the removal of endometriosis, preventing de-novo adhesion formation, treatment of ectopic pregnancy, myomectomy of uterus or fundus, and hysterectomy.

Musculoskeletal surgeries, including fibrosis of joints resulting from traumatic injury, such as a fall or collision, which may render the injured joint stiff and movement painful, in part because scar tissue may form in the traumatized area after tendon damage. These procedures include temporomandibular joint dysfunction, wherein jaw movement is limited and may be painful.

Currently, these joint lesions are treated by opening the joint surgically, or accessing the joint arthroscopically, and removing the adhesions. This treatment has the disadvantage of inducing further fibrosis during the healing process. The compositions and methods of the present disclosure inhibit subsequent fibrosis and adhesion formation in the joint, thus increasing the chance of successful therapy.

Thoracic surgeries, including sternectomy which can be hazardous after primary surgery because of adhesion formation between the heart or aorta and sternum, bypass anastomosis, and heart valve replacement.

Cranial surgeries, including adhesions involving the skull, dura and cortex can complicate the secondary procedures.

Ocular surgeries, including strabismus surgery, glaucoma filtering surgery, and lacrimal drainage system procedures.

Oral surgeries, including the treatment of temporomandibular joint dysfunction.

Other applications that may benefit from the inhibition of scar formation and fibrosis include the following implanted devices: nephrostomy tube, peritoneal drainage tube, artificial hip joint, artificial heart valve, peripheral nerve repair and other prostheses and intravenous catheter. Implants may be treated by coating or impregnating the implant, or a portion thereof, with a composition provided by the present disclosure. The present disclosure may also provide for an improved implant, in which the improvement comprises a coating on the implant, which coating consists of a suitable amount of an inhibitory-adhesive composition.

The compositions and methods of the present disclosure can also be fashioned into tissue adhesives and sealants which may be useful for medical and veterinary applications, including, but not limited to, wound closure, supplementing or replacing sutures or staples in internal surgical procedures such as intestinal anastomosis and vascular anastomosis, tissue repair, preventing leakage of fluids such as blood, bile, gastrointestinal fluid and cerebrospinal fluid, ophthalmic procedures, and drug delivery.

In one embodiment, the hydrogel tissue adhesive of the disclosure may also be used to bond at least two anatomical sites together. In this embodiment, the first aqueous solution or dispersion is applied to at least one anatomical site, and the second aqueous solution or dispersion is applied to at least one of either the same site or one other site using the methods described above. The two or more sites are contacted and held together manually or using some other means, such as a surgical clamp, for a time sufficient for the mixture to cure. Alternatively, a mixture of the two aqueous solutions or dispersions is applied to at least one of the anatomical sites to be bonded using methods described above. The two or more sites are contacted and held together manually or using some other means, such as a surgical clamp, for a time sufficient for the mixture to cure.

In another embodiment, the aldehyde-functionalized dextran, and the multi-arm polyethylene glycol amine may be used in the form of finely divided powders. The powders may be prepared using any suitable method. For example, each of the aqueous solutions or dispersions described above may be dried using heat, vacuum, a combination of heat and vacuum, or by lyophilization, to form powders. Optionally, the powders may be comminuted into finer particles using methods known in the art including, but not limited to, grinding, milling, or crushing with a mortar and pestle. The finely divided powders may be sterilized using the methods described above. The finely divided powders may be applied to an anatomical site on tissue of a living organism in a variety of ways. For example, the powders may be individually applied to the site in any order by sprinkling or spraying. Additionally, the powders may be premixed and the resulting mixture applied to the site by sprinkling or spraying. The powders may be hydrated on the site by the addition of an aqueous solution such as water or a suitable buffer (e.g., phosphate-buffered saline) or by the physiological fluids present at the site. The finely divided powders may also be used to bond two anatomical sites together as described above for the aqueous solutions or dispersions. Alternatively, the powders may be hydrated with water or a suitable aqueous solution prior to use to form the first and second aqueous solutions or dispersions, described above.

The disclosure of all references cited in the present disclosure are herein incorporated by reference in their entirety.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions.

REAGENT PREPARATION

Preparation of Dextrans Having Pendant Aldehyde Groups (AFD-15-177-115% and AFD-10-216-94%)

Dextran containing pendant aldehyde groups and having a weight-average molecular weight of about 10 kDa to about 15 kDa, an equivalent weight per aldehyde group of about 177, and a degree of aldehyde substitution of about 115% was prepared using a two-step procedure. In the first step, dextran having an average molecular weight of about 8.5-11.5 kDa was reacted with glycidol to form alkylated dextran. In the second step, the alkylated dextran was oxidized with sodium periodate to oxidize the terminal diol groups added in the first step to give dextran having pendant aldehyde groups.

In the first step, 350 g of dextran (average molecular weight of about 8.5-11.5 kDa, Sigma-Aldrich, Milwaukee, Wis.) was suspended in 385 mL of water and heated to 55° C. To this solution was added 437 mL of sodium hydroxide solution (20 wt % in water), followed by the slow addition (4.5 mL/min) of glycidol (637 g, Aldrich) over a 2 hour period at 55° C. Then, the mixture was maintained at 55° C. for an additional 2 hours, after which the reaction mixture was cooled to room temperature and allowed to stir slowly for an additional 12 hours. The resulting yellow homogeneous mixture was neutralized with 50% HCl (final pH was 6.6). The sample was precipitated in approximately 5× volume of cold isopropanol (~0° C.). The isopropanol layer was decanted off, the solid product washed with cold isopropanol, and the process of dissolution followed by precipitation was repeated two more times. Three hundred grams of the crude material (containing roughly 75 g of isopropyl alcohol) was transferred to a round bottom flask and rotovapped for approximately 2 hours to remove excess isopropyl alcohol. The material was dissolved in 2 L of deionized water and purified on a TFF system (tangential flow filtration column), with a molecular weight cutoff of 3,000 MW (Millipore Corp., Billerica, Mass.). The sample was run on the TFF system with 7 exchanges; 219 g of material was recovered.

In the second step, 219 g of the solid product from the first step was dissolved in 2,025 mL of water in a round bottom flask and then the resulting solution was cooled to 7-8° C. Sodium periodate solution (2,190 g in 2,354 mL of water) was added to the round bottom flask dropwise over 60 min, the reaction mixture was stirred an additional 30 min after the addition was completed, and then cooled to 0° C. to precipitate residual sodium periodate and filtered. The filtrate was collected in a 12 L multineck flask. To the filtrate was added 158.4 g of calcium chloride followed by addition of 107.3 g of potassium iodide, resulting in the formation of a reddish brown solution, which was stirred for 20 min. To this mixture, acetone was added at 3× volume to precipitate the solids and the mixture was stirred for an additional 30 min. The solids were collected by vacuum filtration and washed with additional acetone (approximately 1 L). The washed precipitate was dried under vacuum, and about 254 g of an off-white solid material was recovered.

The product was dissolved in water to about a 12 wt % solution and purified using a TFF system with a 1000 MW cutoff membrane. After 18 volume exchanges, the product was lyophilized to dryness, yielding 100 g of a cream colored solid.

The equivalent weight per aldehyde group of the product was determined by titration of the hydroxylamine adduct using the method described by Zhao and Heindel (*Pharmaceutical Research* 8:400, 1991). Specifically, the equivalent weight (EW) per aldehyde group was determined as follows. The sample was dissolved in water to give a 20 wt % solution. To this solution was added 25 mL of hydroxylamine hydrochloride solution. The resulting mixture was vortexed briefly and then allowed to stand at room temperature for 2 hours. After that time, the solution was titrated with standardized sodium hydroxide solution (0.25 N) until the color of the solution changed from red to yellow, or to that of the starting hydroxylamine hydrochloride solution. Two replicate determinations were done. The equivalent weight per aldehyde group was calculated using the following formula: (Vol in mL of NaOH×N NaOH)×$10^{-3}$ mol/weight of sample)=1/EW. The equivalent weight per aldehyde group was determined to be 177. The degree of aldehyde substitution was calculated assuming that a substitution of 100% corresponds to one pendant aldehyde group per dextran molecule and that the chemical structure of the aldehyde-functionalized dextran is:

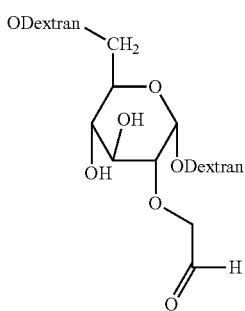

The equivalent weight per aldehyde group of this structure is 204. The degree of aldehyde substitution of the aldehyde-functionalized dextran was then calculated using the following formula: Degree of aldehyde substitution=204/EW (determined as described above)×100. The degree of aldehyde substitution was 115%. The resulting aldehyde-functionalized dextran is referred to herein as AFD-15-177-115% (AFD-MW-EW-degree of aldehyde substitution).

Dextran containing pendant aldehyde groups and having a weight-average molecular weight of about 10 kDa to about 15 kDa and an equivalent weight of about 216 and a degree of aldehyde substitution of about 94% was prepared using the same general method as described above for AFD-15-177-115%. The resulting aldehyde-functionalized dextran is referred to herein as AFD-10-216-94%.

Preparation of Oxidized Dextran (D10-50)

Dextran aldehyde was made by oxidizing dextran having a weight-average molecular weight of about 8.5-11.5 kDa (Sigma-Aldrich) in aqueous solution with sodium metaperiodate. The oxidized dextran, referred to herein as D10-50, had an average molecular weight of about 10,000 Da and an oxidation conversion of about 50% (i.e., about half of the glucose rings in dextran are oxidized to dialdehydes). The oxidation conversion of the oxidized dextran was determined by proton NMR to be about 50% (equivalent weight per aldehyde group=146). In the NMR method, the integrals for two ranges of peaks are determined, specifically, —O$_2$CHx- at about 6.2 parts per million (ppm) to about 4.15 ppm (minus the HOD peak) and —OCHx- at about 4.15 ppm to about 2.8 ppm (minus any methanol peak if present). The calculation of oxidation level is based on the calculated ratio (R) for these areas, specifically, R=(OCH)/(O$_2$CH).

Preparation of Eight-Arm PEG 10K Octaamine (P8-10-1)

Eight-arm PEG 10K octaamine ($M_n$~10 kDa) is synthesized using the two-step procedure described by Chenault in commonly owned U.S. Pat. No. 7,868,132. In the first step, the 8-arm PEG 10K chloride is made by reaction of thionyl chloride with the 8-arm PEG 10K octaalcohol. In the second step, the 8-arm PEG 10K chloride is reacted with aqueous ammonia to yield the 8-arm PEG 10K octaamine. A typical procedure is described here.

The 8-arm PEG 10K octaalcohol ($M_n$=10000; NOF Sun-Bright HGEO-10000), (100 g in a 500-mL round-bottom flask) is dried either by heating with stirring at 85° C. under vacuum (0.06 mm of mercury (8.0 Pa)) for 4 hours or by azeotropic distillation with 50 g of toluene under reduced pressure (2 kPa) with a pot temperature of 60° C. The 8-arm PEG 10K octaalcohol is allowed to cool to room temperature and thionyl chloride (35 mL, 0.48 mol) is added to the flask, which is equipped with a reflux condenser, and the mixture is heated at 85° C. with stirring under a blanket of nitrogen for 24 hours. Excess thionyl chloride is removed by rotary evaporation (bath temp 40° C.). Two successive 50-mL portions of toluene are added and evaporated under reduced pressure (2 kPa, bath temperature 60° C.) to complete the removal of thionyl chloride. Proton NMR results from one synthesis are: $^1$H NMR (500 MHz, DMSO-d6) δ 3.71-3.69 (m, 16H), 3.67-3.65 (m, 16H), 3.50 (s, ~800H).

The 8-arm PEG 10K octachloride (100 g) is dissolved in 640 mL of concentrated aqueous ammonia (28 wt %) and heated in a pressure vessel at 60° C. for 48 hours. The solution is sparged for 1-2 hours with dry nitrogen to drive off 50 to 70 g of ammonia. The solution is then passed through a column (500 mL bed volume) of strongly basic anion exchange resin (Purolite® A-860, The Purolite Co., Bala-Cynwyd, Pa.) in the hydroxide form. The eluant is collected and three 250-mL portions of de-ionized water are passed through the column and also collected. The aqueous solutions are combined, concentrated under reduced pressure (2 kPa, bath temperature 60° C.) to about 200 g, frozen in portions and lyophilized to give the 8-arm PEG 10K octaamine, referred to herein as P8-10-1, as a colorless waxy solid.

Preparation of 8-Arm PEG 10K Hexadecaamine (P8-10-2)

An 8-arm PEG 10K hexadecaamine, referred to herein as "P8-10-2", having two primary amine groups at the end of the arms, was prepared using a two-step procedure, as described by Arthur in U.S. Pat. No. 8,282,959, in which 8-arm PEG 10K was reacted with methanesulfonyl chloride in dichloromethane in the presence of triethylamine to produce 8-arm PEG 10K mesylate, which was subsequently reacted with tris(2-aminoethyl)amine to give the 8-arm PEG 10K hexadecaamine. A typical synthesis is described here.

To a solution of 10 g of 8-arm PEG 10K ($M_n$=10,000; NOF, Tokyo, Japan) in 50 mL of dichloromethane stirred under nitrogen and cooled to 0° C. is added 2.2 mL of triethylamine, followed by 1.2 mL of methanesulfonyl chloride. The mixture is allowed to warm to room temperature and is stirred overnight. The reaction mixture is transferred to a separatory funnel and washed gently three times with 15 mL portions of 1 M potassium dihydrogen phosphate, followed by 15 mL of 1 M potassium carbonate, and then 15 mL of water. The dichloromethane layer is dried over magnesium sulfate, filtered, and concentrated by rotary evaporation to afford 11.17 g of 8-arm PEG 10K mesylate.

A mixture of 10 g of 8-arm PEG 10K mesylate and 45 mL of tris(2-aminoethyl)amine dissolved in 45 mL of water is stirred at room temperature for 24 hours. The reaction mixture is diluted with 45 mL of 5% (w/w) aqueous sodium bicarbonate and extracted with a total of 500 mL of dichloromethane divided in 3 portions. The dichloromethane solution is dried over sodium sulfate, and concentrated by rotary evaporation to 20-25 g. Ether (100 mL) is added to the concentrated dichloromethane solution with vigorous stirring, and the mixture is cooled to 0° C., causing a waxy solid to separate from solution. The solvent is decanted from the waxy solid, and the waxy solid is dried under vacuum to give the 8-arm PEG 10K hexadecaamine (P8-10-2).

Examples 1-5

Low Swell Hydrogels

The purpose of these Examples was to demonstrate the low swell property of the hydrogels disclosed here.

Hydrogels were formed by mixing two aqueous solutions, the first aqueous solution containing the aldehyde-functionalized dextran (AFD-15-177-115%) and 300 ppm of FD&C Blue #1 dye, and the second aqueous solution containing a polyethylene glycol amine (P8-10-1). The two aqueous solutions were mixed using a dual barrel syringe with a 16 stage mixing tip (MEDMIX SYSTEMS AG, Rotkreuz, Switzerland). The concentrations of the aqueous solutions used are given in Table 1. The resulting mixture was injected directly into a piece of plastic tubing having an internal diameter of about 4 mm. After gelation, the hydrogel was removed from the tubing by slitting the tubing open. The resulting cylindrical hydrogel was cut into pieces having a length of approximately 10 mm and each piece was placed inside a separate piece of plastic tubing, which had an internal diameter of about 5 mm and a length of about 20 mm. The length of each hydrogel piece was measured using a ruler to the nearest 0.5 mm, and then each piece of tubing was placed into a separate 20 mL glass vial containing phosphate-buffered saline (PBS). The vials were capped and the lids were sealed with tape. Then, the vials were placed in an incubator at 37° C. on their sides to maintain the hydrogels in a horizontal position. The vials were removed from the incubator at intervals, the length of the hydrogels was measured as described above, and then the vials were returned to the incubator.

The results are summarized in Table 1 as the mean and standard deviation of the swell, where the swell is the percentage increase in the length of the hydrogel relative to its initial length. The negative swell values in the table indicate that the hydrogel decreased in length. All compositions of the present disclosure exhibit "low swell" as defined herein as having a % swell of less than about 2% as measured by this technique.

TABLE 1

Swell of Hydrogels

| Example | Aldehyde-Functionalized Dextran Solution | Multi-Arm PEG amine solution | Day | Swell (%) |
|---|---|---|---|---|
| 1 | AFD-15-177-155% 10 wt % | P8-10-1 15 wt % | 1 | −17 ± 6 |
| | | | 2 | −24 ± 10 |
| | | | 4 | −21 ± 14 |
| | | | 7 | −26 ± 11 |
| | | | 10 | −26 ± 11 |
| | | | 14 | −19 ± 15 |
| | | | 28 | −37 ± 16 |
| 2 | AFD-15-177-115% 20 wt % | P8-10-1 15 wt % | 1 | 6 ± 8 |
| | | | 2 | 1 ± 3 |
| | | | 4 | −1 ± 5 |
| | | | 7 | 0 ± 4 |
| | | | 10 | −7 ± 5 |
| | | | 14 | −5 ± 7 |
| | | | 28 | −6 ± 6 |
| 3 | AFD-15-177-115% 15 wt % | P8-10-1 17.5 wt % | 1 | 5 ± 6 |
| | | | 2 | 3 ± 5 |
| | | | 4 | 8 ± 5 |
| | | | 7 | 2 ± 3 |
| | | | 10 | −1 ± 2 |
| | | | 14 | 2 ± 3 |
| | | | 28 | 1 ± 6 |
| 4 | AFD-15-177-115% 10 wt % | P8-10-1 20 wt % | 1 | −6 ± 6 |
| | | | 2 | −4 ± 5 |
| | | | 4 | 2 ± 9 |
| | | | 7 | −2 ± 9 |
| | | | 10 | −2 ± 9 |
| | | | 14 | −7 ± 12 |
| | | | 28 | −25 ± 23 |
| 5 | AFD-15-177-115% 15 wt % | P8-10-1 15 wt % | 1 | 0 ± 7 |
| | | | 2 | −6 ± 6 |
| | | | 4 | 0 ± 7 |
| | | | 7 | −3 ± 9 |
| | | | 10 | −3 ± 9 |
| | | | 14 | −4 ± 12 |
| | | | 28 | −11 ± 7 |

Comparative Examples 1-6

Hydrogels were prepared as described in Comparative Examples 1-6 using a first aqueous solution comprising AFD-15-177-115% or an oxidized dextran (D10-50), prepared as described above, and a second aqueous solution comprising P-8-10-1 or a mixture of P8-10-1 and P-8-10-2, as indicated in Table 2. In addition, hydrogels were formed using a commercially available product, DuraSeal™ Dural Sealant (COVIDEAN, Mansfield, Mass.). The swell of the hydrogels was measured as described in Examples 1-5. The results are presented in Table 2.

TABLE 2

Swell of Comparative Hydrogels

| Comparative Example | Dextran Solution | Multi-Arm PEG amine solution | Day | Swell (%) |
|---|---|---|---|---|
| 1 | AFD-15-177-115% 20 wt % | P8-10-1 20 wt % | 1 | 11 ± 1 |
| | | | 2 | 15 ± 7 |
| | | | 4 | 15 ± 7 |
| | | | 7 | 14 ± 5 |
| 2 | AFD-15-177-115% 15 wt % | P8-10-1 (15 wt %)/ P8-10-2 (5 wt %) | 1 | 37 ± 10 |
| | | | 2 | 40 ± 11 |
| | | | 6 | 42 ± 10 |
| 3 | AFD-15-177-115% 20 wt % | P8-10-1 (15 wt %)/ P8-10-2 (5 wt %) | 1 | 39 ± 8 |
| | | | 2 | 39 ± 8 |
| | | | 6 | 33 ± 9 |
| 4 | AFD-15-177-115% 15 wt % | P8-10-1 30 wt % | 1 | 84 ± 7 |
| | | | 2 | 74 ± 12 |
| | | | 6 | 85 ± 10 |
| 5 | AFD-15-177-115% 15 wt % | P8-10-1 40 wt % | 1 | 76 ± 5 |
| | | | 2 | 81 ± 7 |
| | | | 6 | 87 ± 9 |
| 6 DuraSeal ™ | NA | NA | 1 | 48 ± 5 |
| | | | 2 | 37 ± 7 |
| | | | 6 | 47 ± 5 |

As can be seen by comparing the data in Table 1 with the data in Table 2, the hydrogels disclosed herein have significantly lower swell than the comparative hydrogels.

Example 6

In Vivo Adhesion Prevention in a Rabbit Laminectomy Model

The compositions of the present disclosure were tested to determine their effectiveness in preventing the formation of deleterious fibrous tissues in a Rabbit Laminectomy study. Two low swell compositions (i.e., Examples 1 and 5) were evaluated for adhesion prevention in a rabbit dorsal laminectomy model.

Aqueous solutions of AFD-15-177-115% (10 wt % and 15 wt %) and P8-10-1 (15 wt %) were prepared and sterilized as follows. The appropriate weight of each component was calculated and adjusted for moisture content (as measured using a Mettler Toledo HB43-S moisture analyzing balance). This amount was weighed into a glass vessel and the calculated weight of water was added. A volume of a stock solution of FD&C Blue #1 dye was added to each of the AFD-15-177-115% solutions to give a final concentration of 300 ppm. The resulting solutions were capped and placed on a shaker incubator at 170 rpm and 40° C. until the components where fully dissolved. These solutions were then filtered through 0.45 μm membrane filters and stored at room temperature until syringe fill.

Twelve dual barreled, 5 mL syringes were prepared by placing pistons in the bottom of each syringe and using the appropriate plunger to evenly position the plungers in the barrels. The syringes (12), plungers (12), caps (12) and 16-step tapered mix tips (30) (MEDMIX SYSTEMS AG) were placed into sterilization pouches and steam sterilized in an autoclave set to a standard "hard goods" cycle. Also sterilized were 4 blunt ended leur-type stainless steel transfer cannulas and two sets of sterilization pouches and labels for packaging. A biological hood was prepared for the sterile fill procedure by thoroughly wiping down all surfaces with a disinfectant and exposing all of the cabinet inner surfaces to UV light for 30 min. The bottles containing the aqueous solutions were sprayed and wiped down with 100% ethanol prior to transfer into the biological hood. These solutions were sterile filtered through pre-sterilized 0.2 µm filters into pre-sterilized containers. The pre-sterilized syringes and packaging materials were then transferred into the biological hood. Six syringes were filled with each solution. The AFD-15-177-115% solution was filled first into the un-notched side of the dual barreled syringes and then the P8-10-1 solution was filled into the notched side of the syringe. The syringes were capped, labeled, and placed in a pre-sterilized pouch with a plunger and two or three of the 16-step mix tips and the pouch was sealed. Each primary pouch was then labeled and placed into a secondary pre-sterilized pouch and that pouch was sealed. This procedure provided a system where the primary sterile pouch can be placed onto the sterile surgical field from the secondary pouch without compromising the sterile field. All materials were stored at room temperature until use.

Twelve New Zealand White Rabbits were used in the study, six for each of the two compositions tested. Each rabbit had two laminectomy sites, L2 & L4, one treated with one of the low swell hydrogel compositions and one untreated control. The treatment site location was randomized within each treatment group. The laminectomy created an approximately 5 mm×10 mm exposure of the spinal cord. A mixture of the first aqueous solution containing AFD-15-177-115% and the second aqueous solution containing P8-10-1 was applied to cover the defect at the treatment site using a dual barrel syringe with a 16 stage mixing tip. The average application dose was 0.08 g. At necropsy after 28 days, each site was examined and graded for adhesions with the following scales:

Adhesion Extent of Total Area. 0: None (no adhesions); 1: 1-25%; 2: 26-50%; 3: 51-75%; 4: 76-100%. The adhesion extent is the amount of the original Laminectomy area covered with scar tissue.

Adhesion Severity Scoring. 0: None (no adhesions); 1: One thin filmy adhesion, non-adherent; 2: Definite adhesions, blunt dissection required; 3: Dense adhesions, sharp dissection required.

Two control sites and three treated sites had boney tissue growth over the defect site, and were therefore unable to be graded for adhesions. All tissues were collected and sent for pathological and histological evaluation.

ANOVA analysis of the Adhesion Total Score (AD_TS=Adhesion Severity+Adhesion Extent), versus group and site showed that both low swell hydrogel compositions gave equal results and both treatment sites were equivalent. Therefore, the scores obtained with both compositions were combined. All the control sites had dense adhesions to the spinal cord with AD_TS≥6.

The ANOVA analysis results for combined treated sites and control sites versus the responses of adhesion extent, adhesion severity and adhesion total score are shown in Table 3. The combined treated sites were 56% adhesion free, 22% had AD_TS≤2 and the last 22% had AD_TS≥6. The average adhesion severity and extent scores had reductions over the control group of 70 and 71%, respectively. These results are surprisingly superior to the published results with existing commercial DuraSeal™ (e.g., Mo et al., "Evaluation of Perivascular Adhesion Formation in New Zealand White Rabbits Using Oxiplex and DuraSeal Xact Adhesion Barrier System" SAS Journal, 3(2), 76, June 2009).

TABLE 3

ANOVA Analysis of Adhesions

| Response | Treated Sites Ave ± Std Dev (n = 10) | Control Sites Ave ± Std Dev (n = 11) | P Value |
| --- | --- | --- | --- |
| Adhesion Extent (0-4) | 0.9 ± 1.3 | 3.0 ± 0 | 0.000 |
| Adhesion Severity (0-3) | 1.0 ± 1.5 | 3.4 ± 0.96 | 0.001 |
| Adhesion Total Score | 1.9 ± 2.8 | 6.4 ± 1.0 | 0.000 |

The hemostatic properties of the low swell hydrogel compositions disclosed herein were also demonstrated in this study with rabbit no. 8. This rabbit bled severely during the first (L2) laminectomy. The surgeon was going to sacrifice this rabbit but instead, a mixture of the first and second aqueous solutions were applied to the laminectomy site at twice the dose used in the other rabbits. The bleeding stopped to the extent that the animal survived and the second laminectomy site was completed as a control site. This treatment site showed no signs of adhesions at 28 days.

Example 7

Cytotoxicity Testing

The two compositions described in Examples 1 and 5 were tested for cytotoxicity using dilutions of the component aqueous solutions and extracts from the hydrogel using three cell lines.

The cell lines (purchased from American Type Culture Collection Manassas, Va.) used in the cytotoxicity testing were L929 (ATCC#CCL-1) cell line as per ISO 109933; MG63 (ATCC#CRL-1427) osteosarcoma derived cell line; and S16 (ATCC#CRL-2941) nerve cell line derived from Schwann cells.

Cell Preparation/Cell Maintenance

Cells were cultured in T-75 (75 cm$^2$) flasks containing 10 mL of the appropriate medium (Eagle's Minimum Essential Medium plus 10% horse serum and penicillin/streptomycin for L929; Eagle's Minimum Essential Medium plus 10% heat-inactivated fetal bovine serum and penicillin/streptomycin for MG-63; and Dulbecco's Modified Eagle's Medium plus 10% fetal bovine serum for S16). After reaching 80-90% confluence, the cells were sub-cultured into new T-75 flasks at the suggested splitting ratio.

Preparation of Assay Plates (96 Well) Containing Cells

For each flask, the medium was removed and the cell layer was washed with 5 mL of PBS (phosphate-buffered saline). The PBS was discarded and 1.5 mL of trypsin was added per flask. The trypsin was gently rocked in the flask to allow equal dispersion across the cell layer until the cells were detached from the flask surface. To the trypsin-cell suspension, 8.5 mL of complete medium was added to inactivate the trypsin and provide a homogeneous cell suspension. The suspension was placed into a sterile 15 mL tube and centrifuged at 130×g for 10 min. After centrifugation, the medium was removed and 10 mL of fresh medium was added to the tube. The cells were re-suspended by mild titration until a homogeneous suspension was obtained.

To a clean 1.5 mL microfuge tube, 300 μL of PBS, 500 μL 0.4% Trypan Blue Stain solution, and 200 μL of the cell suspension were added and the resulting suspension was mixed thoroughly and then allowed to stand for 5 min.

A hemocytometer (Hausser Scientific, Horsham, Pa.) was set up with the cover glass in place. The cell suspension was mixed and an aliquot was added to the hemocytometer, which was then placed onto the stage of a microscope and the number of cells was counted in each of the eight blocks. The number of cells per mL of suspension was calculated by averaging the number of cells in the eight blocks and multiplying by $5 \times 10^6$. To obtain the volume of the cell suspension to add to each well, the number of cells desired for each well was divided by the number of cells per mL of cell suspension. Fresh medium was added to each well of the 96-well plate (volume of fresh medium=200 μL–volume of cell suspension). Next, the volume of cell suspension to give the proper cell number per well for each cell type was added to each well (i.e., for L929, 25,000 cells/well; for MG63, 2,000 cells/well; and for S16, 15,000 cells/well) and the plates were incubated for 24 h at 37° C. with 5% $CO_2$.

Sample Preparation for Soluble Components

Samples of AFD-15-177-115% and P8-10-1, 100 mg each, were weighed into separate clean glass vials (20 mL) and the final weight was brought to 1.0 g with sterile water, giving a final of concentration of 10 wt %. The vials were capped and placed in a 37° C. shaker at 170 rpm for 1 hour to dissolve the samples. When the samples were completely dissolved, the solutions were sterile filtered into sterile glass vials using a 0.2 μm syringe filter. Dilutions of these solutions were prepared using the complete medium of each cell type to be assayed with a minimum final volume of 800 μL or enough to allow for 200 μL/well with a minimum of 200 μL excess. The dilutions were made in sterile microfuge tubes to yield concentrations of 10, 5, 2.5, 1, 0.5, 0.1, 0.05 and 0 mg/mL.

Hydrogel Samples for MEM (Minimum Essential Medium) Elution

Hydrogels were produced using sterile double barrel syringes fitted with a six stage mixer and 1 mL of each sterile aqueous solution in the syringe (i.e., AFD-15-177-115% (10 wt %) and P8-10-1 (15 wt %)) in separate barrels of one syringe and AFD-15-177-115% (15 wt %) and P8-10-1 (15 wt %) in separate barrels of a second syringe. The hydrogel was formed by dispensing the mixed aqueous solutions (1.0 g) from the double barrel syringe into a sterile glass slide mold. The hydrogel formed was extracted with MEM (a ratio of 0.1 g gel/mL MEM) at 37° C. and 15 rpm for 24 h. The extracted MEM was placed in sterile tubes and diluted with MEM to give extract percentages of 90, 75, 50, 25, 12.5, 6.25, and 0. A volume of 200 μL was added to each PBS washed well containing cells in triplicate following the assay protocol described below.

Assay Procedure

The 96-well plates were removed from the incubator and placed in a biological hood. The medium was removed from the wells and the cell layer was washed 3 times with PBS. After the washes, the PBS was removed and 200 μl of the designated sample was added to the well in triplicate. The plates were then placed back into the incubator and cultured for 48 hours.

Cell Proliferation Assay Using Tetrazolium Dye

The 96-well plates containing cells were placed in a biological hood and the medium was removed. The cells were then carefully washed 3 times with sterile PBS. After the last wash when the PBS was removed, 200 μL of sample dilutions were added to the wells in triplicate. The plates were covered and returned to the incubator for 24 hours. At the end of the incubation period, the plates were removed from the incubator and pictures were taken of representative wells containing the samples and the controls. Then, the medium was removed and the cells were washed 3 times with PBS. Phenol-Red free medium (100 μL) and then 10 μL of WST8 reagent (Cayman Chemical Company, Ann Arbor, Mich.) was added to each well. The solution in the wells was gently mixed by tapping the plate and the plate was returned to the incubator for 2 hours to allow the reaction to occur. At the end of the reaction period, the plate was removed from the incubator and 90 μL of the well contents was transferred to a clean 96-well plate. The plate was placed into a spectrophotometer and the absorbance was read at 450 nm.

The results are shown in Tables 4-6. In the ISO testing with L929 cells, all the gel formulations passed with undiluted extracts (see Table 4). The AFD-15-177-115% component was only toxic at very high concentrations which are not obtainable in the formed hydrogels. The MG63 cell line was highly tolerant to all the hydrogel components, as shown in Table 5. The S16 cell line was the most sensitive cell line. The results with the S16 cell line (Table 6) indicated that lowering the AFD-15-177-115% content in the composition lowers the risk of negatively affecting nerve cells exposed to these compositions.

TABLE 4

Cell Viability of L929 Cells with Soluble Components and Hydrogel Extracts

| | Soluble Component | | Hydrogel Extract | |
|---|---|---|---|---|
| | | | P8-10-1 (15 wt %)/ AFD-15-177- 115% (10 wt %) | P8-10-1 (15 wt %/ AFD-15177- 115% (15 wt %) |
| mg/mL | P8-10-1 | AFD-15-177- 115% | | |
| 10 | 105 ± 7 | 12 ± 1 | 98 ± 2 | 98 ± 8 |
| 5 | 106 ± 4 | 88 ± 2 | 104 ± 5 | 104 ± 9 |
| 2.5 | 111 ± 7 | 102 ± 1 | 107 ± 8 | 110 ± 9 |
| 1 | 104 ± 6 | 96 ± 3 | 100 ± 2 | 102 ± 7 |
| 0.5 | 100 ± 13 | 102 ± 4 | 108 ± 5 | 110 ± 8 |
| 0.1 | 111 ± 8 | 112 ± 4 | 118 ± 5 | 119 ± 13 |
| 0.05 | 107 ± 2 | 102 ± 3 | 111 ± 8 | 105 ± 12 |
| 0 | 100 ± 0 | 100 ± 0 | 100 ± 0 | 100 ± 0 |

TABLE 5

Cell Viability of MG16 Cells with Soluble Components and Hydrogel Extracts

| | Soluble Component | | Hydrogel Extract | |
|---|---|---|---|---|
| | | | P8-10-1 (15 wt %)/ AFD-151-77- 115% (10 wt %) | P8-10-1 (15 wt %/ AFD-15-177- 115% (15 wt %) |
| mg/mL | P8-10-1 | AFD-15-177- 115%8 | | |
| 10 | 100 ± 7 | 97 ± 11 | 79 ± 8 | 74 ± 11 |
| 5 | 107 ± 13 | 107 ± 6 | 89 ± 5 | 81 ± 17 |
| 2.5 | 113 ± 15 | 114 ± 4 | 97 ± 4 | 89 ± 11 |
| 1 | 116 ± 16 | 114 ± 7 | 102 ± 7 | 97 ± 20 |

TABLE 5-continued

Cell Viability of MG16 Cells with Soluble Components and Hydrogel Extracts

| | | Hydrogel Extract | |
|---|---|---|---|
| | Soluble Component | P8-10-1 (15 wt %)/ AFD-151-77- | P8-10-1 (15 wt %/ AFD-15-177- |
| mg/mL | P8-10-1 | AFD-15-177- 115%8 | 115% (10 wt %) | 115% (15 wt %) |
| 0.5 | 118 ± 9 | 124 ± 3 | 106 ± 3 | 98 ± 21 |
| 0.1 | 110 ± 8 | 114 ± 1 | 102 ± 4 | 94 ± 22 |
| 0.05 | 99 ± 6 | 101 ± 1 | 93 ± 3 | 84 ± 13 |
| 0 | 100 ± 0 | 100 ± 0 | 100 ± 0 | 100 ± 0 |

TABLE 6

Cell Viability of S16 Cells with Soluble Components and Hydrogel Extracts

| | | Hydrogel Extract | |
|---|---|---|---|
| | Soluble Component | P8-10-1 (15 wt %)/ AFD-15-177- | P8-10-1 (15 wt %/ AFD-15-177- |
| mg/mL | P8-10-1 | AFD-15-177- 115% | 115% (10 wt %) | 115% (15 wt %) |
| 10 | 97 ± 12 | 16 ± 1 | 92 ± 4 | 60 ± 9 |
| 5 | 103 ± 9 | 16 ± 0 | 96 ± 4 | 32 ± 8 |
| 2.5 | 102 ± 9 | 59 ± 0 | 102 ± 5 | 32 ± 20 |
| 1 | 100 ± 2 | 80 ± 2 | 114 ± 4 | 103 ± 1 |
| 0.5 | 100 ± 4 | 94 ± 2 | 120 ± 5 | 112 ± 2 |
| 0.1 | 98 ± 2 | 98 ± 1 | 119 ± 5 | 113 ± 2 |
| 0.05 | 96 ± 2 | 96 ± 4 | 113 ± 1 | 112 ± 2 |
| 0 | 100 ± 0 | 100 ± 0 | 100 ± 0 | 100 ± 0 |

Example 8

Delivery of Low Swell Composition for Use as a Dural Sealant—Dorsal Laminectomy of Lumbar Vertebrae Model The purpose of this study was to evaluate the delivery of a low swell composition of the disclosure to dorsal laminectomy sites in a cadaveric ovine model.

The low swell composition used in this Example was prepared using a first aqueous solution containing AFD-10-216-94% at 10 wt % and 300 ppm of FD&C Blue #1 dye and a second aqueous solution containing P8-10-1 at 15 wt %. The two aqueous solutions were mixed and delivered using a dual barreled syringe equipped with an 8-stage mixing tip (both from MEDMIX SYSTEMS AG). The aqueous solutions were prepared and sterilized as described in Example 6. Two 3-year old female sheep (*Ovis aries*) having an average weight of about 70 g (obtained from Archer Farms, Inc., Darlington, Md.) were used in the study.

Surgical Procedure

In this study, the lumbar vertebrae of the two sheep were isolated and a dorsal laminectomy was performed on each. The laminectomy sites were 3 cm and 4.5 cm. Lumbar vertebrae were isolated by dissection of the surrounding musculature. Laminectomies were performed with Kerrison rongeurs. The two aqueous solutions described above were first mixed and delivered using the dual barreled syringe and mixing tip described above lateral to the spinal cord by deviating the cord with a probe. Subsequently, the two aqueous solutions were mixed and delivered dorsal to the spinal cord filling the entire defect in the dorsal lamina. Following delivery of the solutions to dorsal laminectomy sites in sheep cadaveric lumbar vertebrae, the resulting hydrogel was allowed to set for several minutes and then the vertebrae were cut in cross section at two sites. The distribution of the hydrogel was recorded with digital photography and stored.

Results

The low swell composition and delivery system provided adequate working time for controlled delivery. Insertion of the syringe tip under the dorsal lamina allowed extension of the composition cranially and caudally from the surgical site. The delivery of the composition was enhanced by deviation of the spinal cord laterally with a blunt probe. This allowed the composition to distribute ventrally encompassing the entire circumference of the spinal cord. The results of this in vitro cadaver study showed that the low swell composition was delivered with the syringe and mixing tip around the spinal cord.

Example 9

Non-Survival Sheep Laminectomy Model with Dural Nick

The purpose of this study was to validate the surgical procedure and the delivery of a low swell composition of the disclosure to lumbar laminectomy sites. The ability of the low swell composition of the disclosure to seal small durotomies was also demonstrated.

The low swell composition used in this Example was the same as described in Example 8. A skeletally mature female sheep (*Ovis aries*; age 5 years; weight 61.35 kg; from Archer Farms, Inc.) was used in this study.

Surgical Procedure

An intrathecal catheter was placed to measure CSF pressure and as an access portal to pressurize the subdural space. A dorsal laminectomy was performed on T13-L1, L2-L3 and L5-L6 using Kerrison rongeurs. A durotomy was performed at each site sequentially by making a small nick in the dura using an 18 gauge needle. A small amount of the low swell composition was applied to the dural nick at each laminectomy site sequentially using the dual barreled syringe and allowed to set. Saline with toluidine blue dye was injected into the catheter to assess leakage at the repair site. The procedures were video recorded. Following the leak check, the low swell composition was applied to the entire defect at each site taking care to fill the spinal canal around the cord via slight retraction. The animal was euthanized at the conclusion of the procedure under general anesthesia. Post-operative CT was performed of the lumbar spine. The lumbar spine was examined macroscopically at necropsy and findings were recorded with digital photography.

Results

The results of this non-survival study showed that the low swell composition can be successfully delivered to dorsal laminectomy sites in vivo. Small 18 gauge durotomies were successfully sealed, although there were some inconsistencies due to the shape of the spinal cord and the viscosity of the low swell composition. The low swell composition was also successfully administered to the entire circumference of the spinal cord.

Example 10

Non-Survival Sheep Cranial Durotomy Model

The purpose of this study was to validate the surgical procedure and the delivery of two low swell compositions of the disclosure. The ability of the low swell compositions to seal small durotomies was also demonstrated.

Two low swell compositions were evaluated in this study. The first low swell composition was prepared using a first aqueous solution containing AFD-10-216-94% at 10 wt % and 300 ppm of FD&C Blue #1 dye and a second aqueous solution containing P8-10-1 at 15 wt % (referred to herein as Formulation I). The second low swell composition was prepared using a first aqueous solution containing AFD-10-216-94% at 15 wt % and 300 ppm of FD&C Blue #1 dye and a second aqueous solution containing P8-10-1 at 15 wt % (referred to herein as Formulation II). The aqueous solutions were prepared and sterilized as described in Example 6. The two aqueous solutions were mixed and delivered using a dual barreled syringe equipped with an 8-stage, 12-stage, or 16-stage mixing tip (from MEDMIX SYSTEMS AG), as indicated in Table 7. A 6 year old female sheep (*Ovis aries*; weight 50.9 kg; from Archer Farms, Inc.) was used in this study.

Surgical Procedure

An intrathecal catheter was placed to measure CSF pressure and as an access portal to pressurize the subdural space. Four craniotomies (14 mm diameter) using an Acra Cut DGR-II disposable cranial perforator (ACRA-CUT Inc. Acton, Mass.) were performed in the parietal bone. A 3-4 mm long durotomy was made using an #11 blade at each site. A low swell composition was applied to each craniotomy site, as indicated in Table 7. At the first two sites, a small amount of a low swell composition was applied to the durotomy and allowed to set. CSF pressure was increased by Trendelenberg position. Leakage of CSF at the repair site was assessed and recorded with video. A low swell composition was then applied to the entire craniotomy defect. At the second two sites, the low swell composition was applied to the entire defect initially and leaks were assessed. The two formulations of low swell composition were assessed at different sites and with each mixing tip (i.e., 8, 12 and 16-stage) used. The animal was euthanized under general anesthesia at the conclusion of the procedure. Postoperative cranial CT was performed.

Results

The results are summarized in Table 7.

TABLE 7

Administration of Low Swell Compositions at Each Craniotomy Site

| Craniotomy Site | Low Swell Formulation | Amount | Mixing Tip | Observation |
| --- | --- | --- | --- | --- |
| Site 1, Left Caudal | I | Small[1] | 8-stage | Dural bleeding, no seal |
| | I | Small | 12-stage | Dural bleeding, no seal |
| | I | Half[2] | 12-stage | Dural bleeding, no seal |
| | II | Small, then Full[3] | 12-stage | Dural bleeding, hemorrhage tract |
| Site 2, Left Cranial | II | Small, then Full | 12-stage | Dural seal, bleeding from bone hindered gelation of formulation |
| Site 3, Right Rostral | II | Full | 12-stage | Dural seal, small amout iof bleeding from durotomy which stabilized |

TABLE 7-continued

Administration of Low Swell Compositions at Each Craniotomy Site

| Craniotomy Site | Low Swell Formulation | Amount | Mixing Tip | Observation |
| --- | --- | --- | --- | --- |
| Site 4, Right Caudal | II | Full | 16-stage | Dural seal, larger amount of bleeding from durotomy which stabilized |

[1]2-4 drops of low swell composition to cover durotomy
[2]Craniotomy filled half way with low swell composition
[3]Craniotomy filled with low swell composition The results of this non-survival study demonstrated that the low swell compositions tested can be successfully delivered to cranial durotomy sites in vivo. The craniotomy procedure allowed sufficient surface area to assess dural sealing competency. Small durotomies (2-3 mm) were successfully sealed and challenged with increasing CSF pressure. Increased viscosity of applied low swell compositions applied with the greater stage mixing tips allowed for more rapid adherence and compensation for gravity. Gel time of the low swell compositions was affected by persistent bleeding from the dura or adjacent bone. Gelation of the low swell compositions in a dry environment appears to be critical to establish effective dural sealant properties. Gelation is inhibited by a moist environment from blood and CSF. Minimizing blood and CSF at the application site allowed successful sealing of the durotomy. In cases where a moderate amount of persistent hemorrhage from either the dura or the bone was observed, the low swell compositions were still able to gel, creating an effective dural sealant when challenged with an increase in CSF pressure. The faster crosslinking formulation (Formulation II) provided better results than the slower crosslinking formulation (Formulation I). The number of stages in the mixing tip also influenced the results with the higher staged mix tips giving better results than the lower stage mix tips. This correlates to the increased mixing providing a gel with a higher crosslink density at the time of application. Injection of dye into the intrathecal catheter could not reach the cranial durotomy sites without meeting increased resistance of injection pressure. The postoperative CT allowed visualization of the craniotomy sites and the low swell compositions can be distinguished between bone, air and fluid, but not soft tissue.

What is claimed is:

1. A kit for forming a hydrogel comprising:
   (a) a first aqueous solution or dispersion comprising one or more aldehyde-functionalized dextrans containing pendant aldehyde groups that are attached to dextran via one of the ring hydroxyl groups, said aldehyde-functionalized dextrans having a weight-average molecular weight of about 10,000 to about 20,000 Da and an equivalent weight per aldehyde group of about 226 to about 170 Da; and
   (b) a second aqueous solution or dispersion comprising one or more polyethylene glycols having eight arms, substantially each arm of which is terminated with at least one primary amine group, wherein the polyethylene glycols have a number-average molecular weight of about 9,000 to about 11,000 Da;
   wherein
   (i) the total concentration of the aldehyde-functionalized dextrans containing pendant aldehyde groups in the first aqueous solution or dispersion is about 5 wt % to about 20 wt % and the total concentration of the polyethylene glycols in the second aqueous solution or dispersion is about 10 wt % to about 18 wt %; or (ii) the total concentration of the aldehyde-functionalized dextrans containing pendant aldehyde groups in the first aqueous solution or dispersion is about 5 wt % to about 10 wt % and the total concentration of the polyethylene glycols in the second aqueous solution or dispersion is about 10 wt % to about 20 wt %, wherein the mean swell of samples of a hydrogel formed by mixing the first aqueous solution or dispersion and the second aqueous solution or dispersion is less than 10% as measured by forming a mixture of the first aqueous solution or dispersion and the second aqueous solution or dispersion using a dual barrel syringe with a 16 stage mixing tip, injecting the mixture directly into a piece of plastic tubing having an internal diameter of about 4 mm, allowing the hydrogel to gel, removing the hydrogel from the tubing by slitting the tubing open, thereby obtaining a cylindrical hydrogel, cutting the cylindrical hydrogel into pieces having a length of approximately 10 mm, placing each piece inside a separate piece of plastic tubing with an internal diameter of about 5 mm and a length of about 20 mm, placing each piece of tubing into a separate 20 mL lass vial containing phosphate-buffered saline, capping the lids of the glass vial and sealing the lids with tape, placing the glass vials in an incubator at 37° C. on their sides to maintain the cylindrical hydrogels in a horizontal position, removing the vials from the incubator at intervals, and measuring the length of the hydrogels wherein the swell of a sample is the percentage increase in the length of the hydrogel relative to its initial length, and wherein measurements are performed using a ruler to the nearest 0.5 mm.

2. The kit of claim 1, wherein the aldehyde-functionalized dextrans have an equivalent weight per aldehyde group of about 226 to about 185 Da.

3. The kit of claim 1, wherein the total concentration of the aldehyde-functionalized dextrans containing pendant aldehyde groups in the first aqueous solution or dispersion is about 5 wt % to about 10 wt % and the total concentration of the polyethylene glycols in the second aqueous solution or dispersion is about 10 wt % to about 18 wt %.

4. The kit of claim 1, wherein the aldehyde-functionalized dextrans have a weight-average molecular weight of about 13,000 to about 17,000 Da.

5. The kit of claim 1, wherein the aldehyde-functionalized dextrans have an equivalent weight per aldehyde group of about 222 to about 189 Da.

6. The kit of claim 1, wherein the polyethylene glycols have a number-average molecular weight of about 9,500 to about 10,500 Da.

7. The kit of claim 1, wherein the aldehyde-functionalized dextrans have a weight-average molecular weight of about 15,000 Da and an equivalent weight per aldehyde group of about 177 Da, wherein the polyethylene glycols have a number-average molecular weight of about 10,000 Da, and wherein the total concentration of the aldehyde-functionalized dextrans containing pendant aldehyde groups in the first aqueous solution or dispersion is about 10 wt % and the total concentration of the polyethylene glycols in the second aqueous solution or dispersion is about 15 wt %.

8. The kit of claim 1, wherein the aldehyde-functionalized dextrans have a weight-average molecular weight of about 15,000 Da and an equivalent weight per aldehyde group of about 177 Da, wherein the polyethylene glycols has a number-average molecular weight of about 10,000 Da, and wherein the total concentration of the aldehyde-functionalized dextrans containing pendant aldehyde groups in the first aqueous solution or dispersion is about 15 wt % and the total concentration of the polyethylene glycols in the second aqueous solution or dispersion is about 15 wt %.

9. A dried hydrogel formed by a process comprising the steps of:

combining in a solvent (a) one or more aldehyde-functionalized dextrans containing pendant aldehyde groups, said aldehyde-functionalized dextrans having a weight-average molecular weight of about 10,000 to about 20,000 Da and an equivalent weight per aldehyde group of about 226 to about 170 Da, and (b) one or more polyethylene glycols having eight arms, substantially each arm of the which is terminated with at least one primary amine group, said polyethylene glycols having a number-average molecular weight of about 9,000 to about 11,000 Da, to form a hydrogel;

wherein
(i) the total concentration of the aldehyde-functionalized dextrans containing pendant aldehyde groups in the solvent is about 5 wt % to about 20 wt % and the total concentration of the polyethylene glycols in the solvent is about 10 wt % to about 18 wt %; or
(ii) the total concentration of the aldehyde-functionalized dextrans containing pendant aldehyde groups in the solvent is about 5 wt % to about 10 wt % and the total concentration of the polyethylene glycols in the solvent is about 10 wt % to about 20 wt %; and treating said hydrogel to remove at least a portion of said solvent to form the dried hydrogel, and wherein the mean swell of samples of a hydrogel formed by mixing the first aqueous solution or dispersion and the second aqueous solution or dispersion is less than 10% as measured by forming a mixture of the first aqueous solution or dispersion and the second aqueous solution or dispersion using a dual barrel syringe with a 16 stage mixing tip, injecting the mixture directly into a piece of plastic tubing having an internal diameter of about 4 mm, allowing the hydrogel to gel, removing the hydrogel from the tubing by slitting the tubing open, thereby obtaining a cylindrical hydrogel, cutting the cylindrical hydrogel into Pieces having a length of approximately 10 mm, placing each piece inside a separate piece of plastic tubing with an internal diameter of about 5 mm and a length of about 20 mm, placing each piece of tubing into a separate 20 mL glass vial containing phosphate-buffered saline, capping the lids of the glass vial and sealing the lids with tape, placing the glass vials in an incubator at 37° C. on their sides to maintain the cylindrical hydrogels in a horizontal position, removing the vials from the incubator at intervals, and measuring the length of the hydrogels, wherein the swell of a sample is the percentage increase in the length of the hydrogel relative to its initial length, and wherein measurements are performed using a ruler to the nearest 0.5 mm.

10. The dried hydrogel of claim 9, wherein the aldehyde-functionalized dextrans have an equivalent weight per aldehyde group of about 226 to about 185 Da.

11. The dried hydrogel of claim 9 wherein said dried hydrogel is in the form of a film.

12. A method for applying a row swell coating using the kit according to claim 1 to an anatomical site on tissue of a living organism comprising the steps of:

applying to the site (a) aldehyde-functionalized dextrans containing pendant aldehyde groups, wherein the aldehyde-functionalized dextrans have a weight-average molecular weight of about 10,000 to about 20,000 Da and an equivalent weight per aldehyde group of about 226 to about 170 Da; followed by (b) polyethylene glycols having eight arms, substantially each arm of which is terminated with at least one primary amine group, wherein the polyethylene glycols have a number-average molecular weight of about 9,000 to about 11,000 Da, or (b) followed by (a), or premixing (a) and (b) and applying the resulting mixture to the site before the resulting mixture completely cures; and wherein the weight percent ratio of aldehyde-functionalized dextrans to polyethylene glycols is about 2:1 to about 1:4.

13. The method of claim 12, wherein the aldehyde-functionalized dextrans have an equivalent weight per aldehyde group of about 226 to about 185 Da.

14. The method of claim 12, wherein the weight percent ratio of aldehyde-functionalized dextrans to polyethylene glycols is about 1:1 to about 5:18.

15. The method of claim 12, wherein the aldehyde-functionalized dextrans have a weight-average molecular weight of about 13,000 to about 17,000 Da.

16. The method of claim 12, wherein the aldehyde-functionalized dextrans have an equivalent weight per aldehyde group of about 222 to about 189 Da.

17. The method of claim 12, wherein the polyethylene glycols have a number-average molecular weight of about 9,500 to about 10,500 Da.

18. The method of claim 12, wherein the aldehyde-functionalized dextrans have a weight-average molecular weight of about 15,000 Da and a degree of aldehyde substitution of about 108%, wherein the polyethylene glycols have a number-average molecular weight of about 10,000 Da, and wherein the weight percent ratio of aldehyde-functionalized dextrans to polyethylene glycols is about 1:1.5.

19. The method of claim 12, wherein the aldehyde-functionalized dextrans have a weight-average molecular weight of about 15,000 Da and a degree of aldehyde substitution of about 108%, wherein the polyethylene glycols has a number-average molecular weight of about 10,000 Da, and wherein the weight percent ratio of aldehyde-functionalized dextrans to polyethylene glycols is about 1:1.

20. The method of claim 12, wherein the site is tissue involved in or affected by a surgical procedure.

21. The method of claim 20, wherein the surgical procedure is lumbar laminectomy, laminotomy, discectomy, flexor tendon surgery, spinal fusion, joint replacement or repair, abdominal procedures, gynecological procedures, musculoskeletal surgeries, thoracic surgeries, cranial surgeries, ocular surgeries, oral surgeries or implants.

* * * * *

UNITED STATES PATENT AND TRADEMARK OFFICE
CERTIFICATE OF CORRECTION

PATENT NO. : 10,207,021 B2  
APPLICATION NO. : 15/620745  
DATED : February 19, 2019  
INVENTOR(S) : Lauri L. Jenkins and Robert C. DiLuccio Page 1 of 1

It is certified that error appears in the above-identified patent and that said Letters Patent is hereby corrected as shown below:

On the Title Page

Item (54) Title: please replace "LOW SWEEL TISSUE ADHESIVE AND SEALANT FORMULATIONS" with "LOW SWELL TISSUE ADHESIVE AND SEALANT FORMULATIONS"

Item (72) Inventors: please replace "Robert C. Dilucclo" with "Robert C. DiLuccio"

In the Specification

Column 1, Line 1: please replace "LOW SWEEL TISSUE ADHESIVE AND SEALANT FORMULATIONS" with "LOW SWELL TISSUE ADHESIVE AND SEALANT FORMULATIONS"

In the Claims

Column 33, Line 24: please replace "lass" with "glass"

Column 34, Line 42: please replace "Pieces" with "pieces"

Column 34, Line 62: please replace "row" with "low"

Signed and Sealed this  
Fifteenth Day of October, 2019

Andrei Iancu  
*Director of the United States Patent and Trademark Office*